US007914982B2

(12) United States Patent
Melkonyan et al.

(10) Patent No.: US 7,914,982 B2
(45) Date of Patent: Mar. 29, 2011

(54) METHODS FOR DETECTING PATHOGEN SPECIFIC NUCLEIC ACIDS IN URINE

(75) Inventors: Hovsep Melkonyan, Princeton, NJ (US); Angela Cannas, Arbus (IT); Louis David Tomei, Genazzano (IT); Samuil R. Umansky, Princeton, NJ (US)

(73) Assignee: Trovagene, Inc., San Diego, CA (US)

( * ) Notice: Subject to any disclaimer, the term of this patent is extended or adjusted under 35 U.S.C. 154(b) by 538 days.

(21) Appl. No.: 11/351,799

(22) Filed: Feb. 10, 2006

(65) Prior Publication Data
US 2007/0037181 A1 Feb. 15, 2007

Related U.S. Application Data

(63) Continuation-in-part of application No. 11/137,934, filed on May 25, 2005, now Pat. No. 7,803,929.

(60) Provisional application No. 60/691,186, filed on Jun. 16, 2005.

(30) Foreign Application Priority Data

Feb. 17, 2005 (IT) .............................. RM2005A0068

(51) Int. Cl.
*C12Q 1/68* (2006.01)
*C12P 19/34* (2006.01)
*C07H 21/04* (2006.01)
(52) U.S. Cl. ....... 435/6; 435/91.2; 435/91.5; 435/91.52; 536/24.33

(58) Field of Classification Search .................. None
See application file for complete search history.

(56) References Cited

U.S. PATENT DOCUMENTS

| 5,168,039 | A | 12/1992 | Crawford et al. ........... 536/24.32 |
| 5,631,130 | A | 5/1997 | Leckie et al. .................... 435/6 |
| 5,712,385 | A | 1/1998 | McDonough et al. ...... 536/24.32 |
| 5,731,150 | A | * | 3/1998 | Sandhu et al. .................... 435/6 |
| 6,251,638 | B1 | 6/2001 | Umansky et al. ............ 435/91.2 |
| 6,287,820 | B1 | 9/2001 | Umansky et al. ............ 435/91.1 |

(Continued)

FOREIGN PATENT DOCUMENTS

WO    WO 95/04140    2/1995

(Continued)

OTHER PUBLICATIONS

Sechi, L.A. et al. Molecular and Cellular Probes 11:281-285 (1997).*

(Continued)

*Primary Examiner* — Diana B Johannsen
(74) *Attorney, Agent, or Firm* — Mintz Levin Cohn Ferris Glovsky and Popeo, P.C.; Ivor R. Elrifi; Matthew Pavao

(57) ABSTRACT

The invention is based upon the discovery that small nucleic acids from non-viral pathogens are able to cross the kidney and are present in urine of a subject when the subject is infected with the non-viral pathogen. These transrenal DNAs are especially prevalent at smaller sizes under about 300 bp. Thus the invention provides compositions and methods for the diagnosis of infection of a subject with non-viral pathogens through the detection of transrenal nucleic acids from those pathogens in the urine of the subject.

4 Claims, 10 Drawing Sheets

U.S. PATENT DOCUMENTS

| | | | |
|---|---|---|---|
| 6,368,800 B1 | 4/2002 | Smith et al. | 435/6 |
| 6,492,144 B1 | 12/2002 | Umansky et al. | 435/91.2 |
| 2002/0119478 A1 | 8/2002 | Umansky et al. | 435/6 |
| 2003/0152591 A1 | 8/2003 | Sablon et al. | 424/225.1 |
| 2003/0152982 A1 | 8/2003 | De Beenhouwer et al. | 435/6 |
| 2004/0053264 A1 | 3/2004 | Park | 435/6 |
| 2006/0183107 A1 | 8/2006 | Melkonyan et al. | 435/5 |
| 2006/0183108 A1 | 8/2006 | Melkonyan | 435/5 |

FOREIGN PATENT DOCUMENTS

| | | |
|---|---|---|
| WO | WO 98/54364 | 12/1998 |
| WO | WO 98/58086 | 12/1998 |
| WO | WO 2006/088895 | 8/2006 |
| WO | WO 2006/089203 | 8/2006 |

OTHER PUBLICATIONS

Broccolo, F. et al. Journal of Clinical Microbiology 41(10):4565-4572 (Oct. 2003).*
Aceti et al. (1999), Thorax., 54:145-6.
Achtman et al. (1999), Molecular Microbiology 32:459-470.
Ahern (1995), The Scientist, 9:20-24.
Akopyanz et al. (1992), Nucleic Acids Res. 20:5137-5142.
Alm et al. (1999), Nature 397:176-180.
Al-Yatama et al. (2001), Prenatal Diagnosis, 21:399-402.
Atherton (1997), Gut 40:701-703.
Atherton et al. (1999), Current Microbiology 39:211-218.
Axon (1999), Gut 45(Supp. I): 1-I4.
Barany (1991), Proc. Natl. Acad. Sci. USA, 88:189-193.
Bekkaoui et al. (1996), BioTechniques 20:240-248.
Belli et al. (1998), American Journal Tropical Medicine and Hygiene 58:102-109.
Bickley, et al. (1993), Journal of Medical Microbiology 39:338-344.
Blackwood et al.(2004), Journal of Clinical Microbiology 42:1626-1630.
Blaser et al. (1995), Cancer Research 55:2111-2115.
Botezatu et al. (2000), Clinical Chemistry 46:1078-1084.
Buffone et al. (1991), Clinical Chemistry 37:1945-1949.
Chan et al. (2003), Cancer Research 63:2028-2032.
Clayton et al. (1992), Journal of Clinical Microbiology 30:192-200.
Cover et al. (1994), The Journal of Biological Chemistry 269:10566-10573.
Del Portillo et al. (1991), Journal of Clinical Microbiology 29:2163-2168.
Disch et al. (2003), Transactions of the Royal Society of Tropical Medicine and Hygiene 97:391-395.
Disch et al. (2004), Acta Tropica 92:279-283.
Drago et al. (2002), Journal of Clinical Microbiology 40:4399.
Drobniewski et al., (2003), The Lancet Infectious Diseases 3:141-147.
Echavarria et al. (1998), Journal of Clinical Microbiology, 36:3323-3326.
Elzinga et al. (2004), The Lancet 363:814-819.
Fasanella et al. (2001), Vaccine 19:4214-4218.
Fenves (1985), Clinical Nephrology 23:96-100.
Frasier et al. (1992), Acta Virol., 36:83-89.
Friedlander (1978), Infection and Immunity, 22:148-154.
Gal et al. (2001), Annals New York Academy of Sciences 945:234-238.
Gorman et al. (1991), Molecular and Biochemical Parasitology 45:281-288.
Green et al. (1985), Infection and Immunity 49:291-297.
Haines et al. (1987), Postgraduate Medicine 81:77-79.
Hammer et al. (1992), Journal of Clinical Microbiology 30:54-58.
Hemal et al. (2000), Urology 56:570-574.
Higgins et al. (2003), Applied and Environmental Microbiology 69:593-599.
Ho et al. (1991), Journal of Clinical Microbiology 29:2543-2549.
Ho et al. (2005), Journal American Chemical Society 127:12673-12676.
Hurtle et al. (2004), Journal of Clinical Microbiology 42:179-185.
Jeong et al. (2004), Journal of Medical Virology, 72:281-289.
Kafwabulula et al. (2002), Int. J. Tuberc. Lung Dis. 6:732-737.
Keim et al. (2000), Journal of Bacteriology 182: 2928-2936.
Kleanthous et al. (1991), Molecular Microbiology 5:2377-2389.
Koide et al. (2005), Prenatal Diagnosis 25:604-607.
Kolk et al. (1992), Journal of Clinical Microbiology 30:2567-2575.
Kox et al. (1995), Neurology 45:2228-2232.
Lee et al. (2002), Cell Death and Differentiation 9:53-64.
Leppla (1995), Handbook of Natural Toxins. 8:543-572.
Li et al. (1990), The Lancet 335:1590-1591.
Lichtenstein et al. (2001), Annals New York Academy of Sciences, 945:239-249.
Lo (2000), Clinical Chemistry, 46:1039-1040.
Logan et al., (2004), Manual of Clinical Microbiology, 8th Ed, p. 445-460.
Lu et al. (1999), Journal of Clinical Microbiology 37:772-774.
Maiwald et al. (1995), European Journal of Clinical Microbiology and Infectious Diseases 14:25-33.
Maiwald et al. (1995), Infection 23:173-179.
Marei et al. (2003), Journal of Medical Microbiology 52:331-335.
Marmur et al. (1960), Biochemistry 46:453-461.
McCutchan et al. (1988), Molecular and Biochemical Parasitology 28:63-68.
Mercier et al. (1997), Molecular and Cellular Probes 11:89-94.
Mikesell et al. (2002), ASM News 49:320-322.
Mobley (1996), The American Journal of Medicine 100(Supp. 5A):5A-11S.
Moussa et al. (2000), The Journal of Urology 164:584-588.
Murdock et al. (1996), Clinical Infectious Diseases 23:475-480.
Navarre (2000), Cellular Microbiology 2:265-273.
Oggioni et al. (2002), Journal of Clinical Microbiology 40:3956-3963.
Piersimoni et al. (2002), Journal of Clinical Microbiology 40:4138-4142.
Piersimoni et al. (2003), Journal of Clinical Microbiology 41:5355-5365.
Pornthanakasem et al. (2001), BMC Cancer 1:2.
Poulter et al. (1981), Clinical Nephrology 15:216-220.
Qari et al. (1996), Molecular Phylogenetics and Evolution 6:157-165.
Qi et al. (2001), Applied and Environmental Microbiology 67:3720-3727.
Sarmiento et al. (2003), Journal of Clinical Microbiology 41:3233-3240.
Schürmann et al. (1983), Zbl. Bakt. Hyg., I. Abr. Orig. A 255:120-126.
Seah et al. (1995), Clinical and Diagnostic Virology, 4:113-120.
Shilo et al. (1981), Proc. Natl. Acad. Sci. USA 78:6789-6792.
Su et al. (2004), Journal of Molecular Diagnostics 6:101-107.
Su et al. (2004), Annals New York Academy of Sciences pp. 1022:81-89.
Tamarit et al. (2004), Journal of Clinical Virology 29:308-314.
Tomb et al. (1997), Nature 388:539-547.
Torrea et al. (2005), Journal of Medical Microbiology 54:39-44.
Tummuru et al. (1993), Infection and Immunity 61:1799-1809.
Uchida et al. (1986), Journal of General Microbiology 132:557-559.
Umansky et al. (1981), Biochimica et Biophysica Acta, 655:9-17.
Utting et al. (2002), Clinical Cancer Research 8:35-40.
Valentine et al. (1991), Journal of Clinical Microbiology 29:689-695.
van Vollenhoven et al. (1996), Urol. Res. 24:107-111.
Walker et al. (1994), Nucleic Acids Research 22:2670-2677.
Wang et al. (2004), Clinical Chemistry, 50: 211-213.
Waters et al. (1989), Nucleic Acids Research 17:2135.
Wegmüller et al. (1985), Arch Intern Med. 145:1711-1713.
Welkos (1991), Microbial Pathogenesis 10:183-198.
Zambardi et al. (1995), Molecular and Cellular Probes, 9:91-99.
International Search Report for PCT/US2006/005792, mailed Jan. 22, 2007.
International Search Report for PCT/US2006/005225, mailed Jan. 4, 2007.

* cited by examiner

METHODS FOR DETECTING PATHOGEN SPECIFIC NUCLEIC ACIDS IN URINE

RELATED APPLICATIONS

This application is a continuation-in-part of U.S. Ser. No. 11/137,934, filed on May 25, 2005, now U.S. Pat. No. 7,803,929 which claims priority of Italian Patent Application No. RM2005000068, filed on Feb. 17, 2005, and claims priority of U.S. Ser. No. 60/691,186, filed Jun. 16, 2005, which are incorporated herein by reference in their entireties.

BACKGROUND OF THE INVENTION

There are currently three types of in vitro diagnostic systems widely used for the detection of non-viral pathogens. These are direct culture of the pathogenic agent from the biological sample; immunological assays based on the detection of products or antigens of the infectious agent; and indirect immunological assays that can detect antibodies produced against the infectious agent during infection.

In the first system, the principal disadvantage is that the biological sample must be considered to be at risk for the transmission of the pathogenic agent. In the second and third systems, the disadvantages include sample retrieval that is often invasive and potentially infective sample when collected. In the third system, one major disadvantage is that there is often little possibility of discriminating between past and current infections.

More recently, molecular diagnostic methods have been developed based on the detection of the nucleic acids of the pathogenic agent in the blood or plasma samples, or in the cell cultures, taken from the patient. These assays are generally much more sensitive than the immunological assays. However, they may require the presence of special equipment and qualified personnel. Furthermore, the biological samples—in the case of plasma, blood, or cell cultures—are difficult to store unaltered, except under controlled temperature conditions, and are considered to be biohazardous to personnel who handle them.

Recently, molecular diagnostic methods based on transrenal DNA (Tr-DNA) have been described for monitoring the progress of allogeneic transplants, to diagnose the sex of a fetus, and to detect the presence of tumor markers. (Botezatu et al. Clinical Chemistry 46(8):1078-84 (2000); Su et al. Ann. NY Acad. Sci. 1022:81-89 (2004)) For example, U.S. Pat. No. 6,251,638 describes an analytical method for detecting male fetal DNA in the urine of pregnant women. U.S. Pat. No. 6,287,820 describes a system aimed at the diagnosis of tumors, particularly of adenocarcinomas of the colon and pancreas. U.S. Pat. No. 6,492,144 teaches that the Tr-DNA nucleic-acid analysis method may be used to monitor the progress of allogeneic transplants. The presence of transrenal DNA in urine, in the form of nucleic-acid fragments of fewer than 1000 base pairs was also described in Al-Yatama et al. (2001), *Prenat Diagn,* 21:399-402; and Utting, M., et al. (2002), *Clin Cancer Res,* 8:35-40. Keiko Koide, et al., *Prenat Diagn,* 2005; 25: 604-607; Mengjun Wang, et al., *Clinical Chemistry,* 2004, 50: 211-213; Y.-H. Su, et al., *J. Mol. Diagn.,* 2004, 6: 101-107.

The presence of transrenal DNA has been explained through the apoptosis phenomenon. During cell death most of the nuclear DNA is converted into nucleosomes and oligomers (Umansky, S. R., et al. 1982, *Biochim. Biophys. Acta* 655:9-17), which are finally digested by macrophages or neighboring cells. However, a portion of this degraded DNA escapes phagocytic metabolism, and can be found in the bloodstream (Lichtenstein, A. V., et al. 2001, *Ann NY Acad Sci,* 945:239-249), and, as confirmed in the above-indicated patents, also in urine.

The application of this system to pathogenic microorganism infections has never been studied. Previously, it was only known that prokaryotic DNA could be isolated from urine sediment that contained bacteria (Frasier, et al. 1992, *Acta Virol,* 36:83-89). During a pathogenic infection, prokaryotes and parasites are generally ingested by the cells of the immune system, such as macrophages and dendritic cells. The prokaryotes are then dissolved by the phagolysosome vesicles. The prokaryotic DNA is then released by the cell and a portion of this DNA enters the bloodstream in either of two ways. Either the ingesting cell becomes apoptotic and breaks apart (Navarre, W. V. 2000; *Cell Microbiol* 2:265-273); or the phagolysosome vesicles release the fragments of the prokaryote (including the fragmented DNA) into the bloodstream (Friedlander, A. M. 1978, *Infect Immune* 22:148-154). However, these fragmented nucleic acids have never been detected in the urine of the infected subject.

The instant invention describes a method of detecting the presence of non-viral pathogens in a subject through the detection of DNA sequences from those pathogens in the urine of the subject.

SUMMARY OF THE INVENTION

The invention provides compositions and methods for the diagnosis of an infection of a subject through the detection of the presence of pathogens by the presence of pathogen nucleic acids in a urine sample of the subject. The methods of the invention are also used to validate the diagnosis of an infection of a subject through the detection of the presence of pathogen nucleic acids in a urine sample of the subject, wherein a previous diagnosis has already been performed by a method of this invention or another diagnosis method. The compositions and methods of the invention are also used to determine the efficacy of a treatment of non-viral pathogen infection in a subject by detecting the presence or absence of a nucleic acid of the non-viral pathogen in the urine of the subject. More specifically, the compositions and methods of the invention are used to identify a drug resistant non-viral pathogenic infection in a subject by detecting the presence or absence of a nucleic acid of the non-viral pathogen in the urine of the subject after the subject has been treated for the infection with a drug. The compositions and methods of the invention are also used to determine the likelihood of pathology from the infection of the subject by a non-viral pathogen in a subject at risk therefrom. More specifically, the compositions and methods of the invention may be used to genotype a non-viral pathogen which has infected a subject by detecting and genotyping nucleic acids from the pathogen in the urine of the subject.

The invention provides a method of isolating a nucleic acid from urine, the method comprising providing urine from a subject; separating cells and cell debris from the urine by filtration or centrifugation; adding EDTA and Tris-HCl to the urine; adding a chaotropic salt to the urine; adding a resin, wherein the resin binds the nucleic acid in the presence of the chaotropic salt; removing the resin from the urine; and eluting the nucleic acid from the resin; thereby isolating the nucleic acid from urine. In one embodiment of the method of isolating a nucleic acid from urine, the concentration of EDTA and Tris-HCl after it is added to the urine is about 10 mM, and pH between about 8.0 and about 8.5.

In another embodiment of the method of isolating a nucleic acid from urine, the filtration is performed with a filter with a pore size between about 0.1 μm and about 5.0 μm.

In another embodiment of the method of isolating a nucleic acid from urine, the chaotropic salt is guanidine isothiocyanate. In one aspect of this embodiment, the guanidine isothiocyanate has a concentration after being added to the urine of at least about 3 M, and at most about 6 M.

In another embodiment of the method of isolating a nucleic acid from urine, the resin is constructed of silica.

In another embodiment of the method of isolating a nucleic acid from urine, the subject is a mammal. In one aspect of this embodiment, the mammal is a human.

The invention also provides a method of detecting a non-viral pathogen in a subject comprising detecting the presence of a nucleic acid from the non-viral pathogen in urine of the subject, wherein the non-viral pathogen is selected from *Helicobacter pylori, Mycobacterium tuberculosis, Bacillus anthracis, Plasmodium* species and *Leishmania*species. In one embodiment of the method of detecting a non-viral pathogen in a subject, the method further comprises the step of quantitating the nucleic acid.

In another embodiment of the method of detecting a non-viral pathogen in a subject, the detecting is performed by a method selected from polymerase chain reaction (PCR), nested PCR, semi-nested PCR, hybridization, Single-Strand Conformation Polymorphism analysis (SSCP), ligase chain reaction (LCR), strand displacement amplification (SDA), and pairing with molecular probes that are specific for the non-viral pathogen.

In another embodiment of the method of detecting a non-viral pathogen in a subject, the subject is a mammal. In one aspect of this embodiment, the mammal is a human.

The invention also provides a method for diagnosing a *Helicobacter pylori* infection in a subject, comprising detecting the presence of a *Helicobacter pylori* nucleic acid in a urine sample from the subject, thereby diagnosing the *Helicobacter pylori* infection. In one embodiment of the method for diagnosing a *Helicobacter pylori* infection in a subject, the method further comprises the step of quantitating the nucleic acid.

In another embodiment of the method for diagnosing a *Helicobacter pylori* infection in a subject, the detecting is performed by a method selected from PCR, nested PCR, semi-nested PCR, hybridization, SSCP, LCR, SDA, and pairing with molecular probes that are specific for the non-viral pathogen. In one aspect of this embodiment, a primer set is used in the method, and the primer set comprises a forward primer and a reverse primer. Optionally, the forward primer is selected from SEQ ID NOs: 5, 8, 10, 11, 12 and 15 and the reverse primer is selected from SEQ ID NOs: 6, 7, 9, 13, 14, 16 and 17.

In another embodiment of the method for diagnosing a *Helicobacter pylori* infection in a subject, the *Helicobacter pylori* nucleic acid comprises transrenal DNA.

In another embodiment of the method for diagnosing a *Helicobacter pylori* infection in a subject, the subject is a mammal. In one aspect of this embodiment, the mammal is a human.

In another embodiment of the method for diagnosing a *Helicobacter pylori* infection in a subject, the method further comprises the step of genotyping the *Helicobacter pylori* which infected the subject. In one aspect of this embodiment, the *Helicobacter pylori* is genotyped for the presence of a cag pathogenicity island. In another aspect of this embodiment, the *Helicobacter pylori* is genotyped for the presence of a vacA genotype selected from s1/m1, s1m2, s2m1 and s2m2.

The invention also provides a method for diagnosing a *Mycobacterium tuberculosis* infection in a subject, comprising detecting the presence of a *Mycobacterium tuberculosis* nucleic acid in a urine sample from the subject, wherein the *Mycobacterium tuberculosis* nucleic acid has crossed the kidney barrier and is from cells outside a urinary tract of the subject, thereby diagnosing the *Mycobacterium tuberculosis* infection. In one embodiment of the method for diagnosing a *Mycobacterium tuberculosis* infection in a subject, the method further comprises the step of quantitating the nucleic acid.

In another embodiment of the method for diagnosing a *Mycobacterium tuberculosis* infection in a subject, the detecting is performed by a method selected from PCR, nested PCR, semi-nested PCR, hybridization, SSCP, LCR, SDA, and pairing with molecular probes that are specific for the non-viral pathogen. In one aspect of this embodiment, a primer set is used for the method, wherein the primer set comprises a forward primer and a reverse primer. Optionally, the forward primer is selected from SEQ ID NOs: 34, 37 and 39 and the reverse primer is selected from SEQ ID NOs: 35, 36, 38 and 40.

In another embodiment of the method for diagnosing a *Mycobacterium tuberculosis* infection in a subject, the *Mycobacterium tuberculosis* nucleic acid comprises transrenal DNA.

In another embodiment of the method for diagnosing a *Mycobacterium tuberculosis* infection in a subject, the subject is a mammal. In one aspect of this embodiment, the mammal is a human.

The invention also provides a method for diagnosing a *Bacillus anthracis* infections in a subject, comprising detecting the presence of a *Bacillus anthracis* nucleic acid in a urine sample from the subject, thereby diagnosing the *Bacillus anthracis* infection. In one embodiment of the method for diagnosing a *Bacillus anthracis* infection in a subject, the method further comprises the step of quantitating the nucleic acid.

In another embodiment of the method for diagnosing a *Bacillus anthracis* infection in a subject, the detecting is performed by a method selected from PCR, nested PCR, semi-nested PCR, hybridization, SSCP, LCR, SDA, and pairing with molecular probes that are specific for the non-viral pathogen. In one aspect of this embodiment, a primer set is used for the method, wherein the primer set comprises a forward primer and a reverse primer. Optionally, the forward primer is selected from SEQ ID NOs: 41, 43, 45, 47, 48 and 50 and the reverse primer is selected from SEQ ID NOs: 42, 44, 46 and 49.

In another embodiment of the method for diagnosing a *Bacillus anthracis* infection in a subject, the *Bacillus anthracis* nucleic acid comprises transrenal DNA.

In another embodiment of the method for diagnosing a *Bacillus anthracis* infection in a subject, the subject is a mammal. In one aspect of this embodiment, the mammal is a human.

The invention also provides a method for diagnosing a *Plasmodium* species infection in a subject, comprising detecting the presence of a *Plasmodium* species nucleic acid in a urine sample from the subject, thereby diagnosing the *Plasmodium* species infection. In one embodiment of the method for diagnosing a *Plasmodium* species infection in a subject, the method further comprises the step of quantitating the nucleic acid.

In another embodiment of the method for diagnosing a *Plasmodium* species infection in a subject, the detecting is performed by a method selected from PCR, nested PCR, semi-nested PCR, hybridization, SSCP, LCR, SDA, and pairing with molecular probes that are specific for the non-viral pathogen. In one aspect of this embodiment, a primer set is used for the method, wherein the primer set comprises a forward primer and a reverse primer. Optionally, the forward primer is selected from SEQ ID NOs: 18, 21 and 23 and the reverse primer is selected from SEQ ID NOs: 19, 20 and 22.

In another embodiment of the method for diagnosing a *Plasmodium* species infection in a subject, the *Plasmodium* species nucleic acid comprises transrenal DNA.

In another embodiment of the method for diagnosing a *Plasmodium* species infection in a subject, the subject is a mammal. In one aspect of this embodiment, the mammal is a human.

The invention also includes a method for diagnosing a *Leishmania* species infection in a subject, comprising detecting the presence of a *Leishmania* species nucleic acid in a urine sample from the subject, thereby diagnosing the *Leishmania* species infection. In one embodiment of the method for diagnosing a *Leishmania* species infection in a subject, the method further comprises the step of quantitating the nucleic acid.

In another embodiment of the method for diagnosing a *Leishmania* species infection in a subject, the detecting is performed by a method selected from PCR, nested PCR, semi-nested PCR, hybridization, SSCP, LCR, SDA, and pairing with molecular probes that are specific for the non-viral pathogen. In one aspect of this embodiment, a primer set is used for the method, wherein the primer set comprises a forward primer and a reverse primer. Optionally, the forward primer is selected from SEQ ID NOs: 26, 28, 30, 32 and 51 and the reverse primer is selected from SEQ ID NOs: 24, 25, 27, 29, 31 and 33.

In another embodiment of the method for diagnosing a *Leishmania* species infection in a subject, the *Leishmania* species nucleic acid comprises transrenal DNA.

In another embodiment of the method for diagnosing a *Leishmania* species infection in a subject, the subject is a mammal. In one aspect of this embodiment, the mammal is a human.

The invention also provides a composition for use in the detection of *Helicobacter pylori*, wherein the composition comprises a nucleic acid sequence selected from SEQ ID NOs: 5-17. In one embodiment of the composition for use in the detection of *Helicobacter pylori*, the composition consists of a nucleic acid sequence selected from SEQ ID NOs: 5-17.

The invention also provides a composition for use in the detection of Plasmodium species, wherein the composition comprises a nucleic acid sequence selected from SEQ ID NOs: 18-23. In one embodiment of the composition for use in the detection of *Plasmodium* species, the composition consists of a nucleic acid selected from SEQ ID NOs: 18-23.

The invention also provides a composition for use in the detection of *Leishmania* species, wherein the composition comprises a nucleic acid sequence selected from SEQ ID NOs: 24-33 and 51. In one embodiment of the composition for use in the detection of *Leishmania* species, the composition consists of a nucleic acid selected from SEQ ID NOs: 24-33 and 51.

The invention also provides a composition for use in the detection of *Mycobacterium tuberculosis*, wherein the composition comprises a nucleic acid sequence selected from SEQ ID NOs: 34-40. In one embodiment of the composition for use in the detection of *Mycobacterium tuberculosis*, the composition consists of a nucleic acid selected from SEQ ID NOs: 34-40.

The invention also provides a composition for use in the detection of *Bacillus anthracis*, wherein the composition comprises a nucleic acid sequence selected from SEQ ID NOs: 41-50. In one embodiment of the composition for use in the detection of *Bacillus anthracis*, the composition consists of a nucleic acid selected from SEQ ID NOs: 41-50.

The invention also provides a kit for detecting *Helicobacter pylori* in a urine sample from a subject in need thereof, comprising at least one forward primer selected from SEQ ID NOs: 5, 8, 10, 11, 12 and 15 and at least one reverse primer selected from SEQ ID NOs: 6, 7, 9, 13, 14, 16 and 17, either in the same or separate packaging, and instructions for its use.

The invention also provides a kit for detecting *Mycobacterium tuberculosis* in a urine sample from a subject in need thereof, comprising at least one forward primer selected from SEQ ID NOs: 34, 37 and 39 and at least one reverse primer selected from SEQ ID NOs: 35, 36, 38 and 40, either in the same or separate packaging, and instructions for its use.

The invention also provides a kit for detecting *Bacillus anthracis* in a urine sample from a subject in need thereof, comprising at least one forward primer selected from SEQ ID NOs: 41, 43, 45, 47, 48 and 50 and at least one reverse primer selected from SEQ ID NOs: 42, 44, 46 and 49, either in the same or separate packaging, and instructions for its use.

The invention also provides a kit for detecting *Plasmodium* species in a urine sample from a subject in need thereof, comprising at least one forward primer selected from SEQ ID NOs: 18, 21 and 23 and at least one reverse primer selected from SEQ ID NOs: 19, 20 and 22, either in the same or separate packaging, and instructions for its use.

The invention also provides a kit for detecting *Leishmania* species in a urine sample from a subject in need thereof, comprising at least one forward primer selected from SEQ ID NOs: 26, 28, 30, 32 and 51 and at least one reverse primer selected from SEQ ID NOs: 24, 25, 27, 29, 31 and 33, either in the same or separate packaging, and instructions for its use.

DETAILED DESCRIPTION OF THE INVENTION

Figure 1:
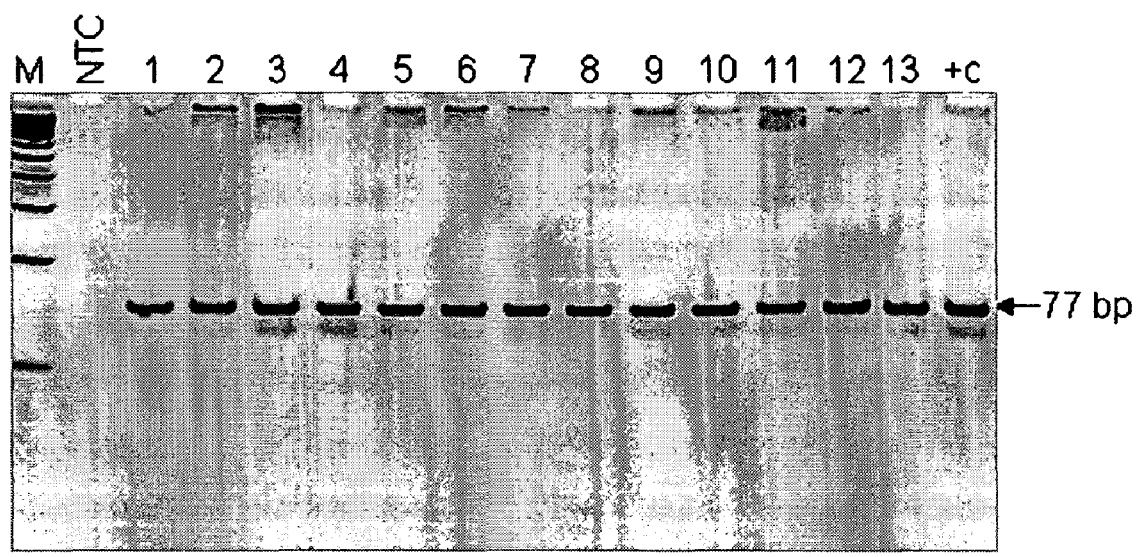
FIG. 1 is a photograph of PCR reactions performed on human urine with primers specifc for human b-actin resolved by electrophoresis.

The invention is based, in part, upon the discovery described herein that pathogenic nucleic acids are detectable in the urine of a subject infected with the pathogen. In some instances, nucleic acids from pathogenic organisms cross the kidney barrier and pass into the urine of mammals. The nucleic acids which cross the renal barrier, termed herein as transrenal nucleic acids, and more specifically transrenal DNA tend to be shorter than 1,000 bp in length, but are preferably less than 500 bp in length, and more preferably shorter than 250-300 bp in length or shorter than 250 bp in length. While it had been shown in the past that DNA from mammalian cells, cancerous and non-cancerous which were hypothesized to die by apoptosis in the body of a subject may be able to cross the renal barrier, this is the first time it has been shown that the DNA of pathogens also crosses this barrier. Further, nucleic acids from pathogens found in the kidney would shed pathogen specific nucleic acids into the urine without crossing the kidney barrier. There may be other mechanisms by which pathogen specific nucleic acids pass into the urine of a subject infected with the pathogen.

Based on this discovery, the invention provides compositions and methods for the detection of non-viral pathogens in the urine of a subject. The compositions and methods of the invention are used to detect transrenal-nucleic acids derived from pathogenic microorganisms which traverse the renal barrier and are present in the urine of a subject. The invention includes methods for the isolation, amplification and detection of these transrenal nucleic acids. The invention also includes compositions which may be used to isolate, amplify these transrenal nucleic acids.

One method of the invention for the isolation of urinary DNA from a subject includes the following steps. Urine is first centrifuged or filtered to separate cells and cell debris from the urine. EDTA/Tris HCl is then added to the urine to bind bivalent ions and to adjust pH to approximately pH 8. To this solution is then added a chaotropic salt, for example guanidine isothiocyanate to a final concentration of at least 3 M. Then a silica resin is added to the urine to which DNA binds. This resin is then washed, and the DNA eluted from it, thereby isolating the transrenal DNA.

DNA isolated from the urine of a subject may then be amplified in order to be detected. Amplification methods include polymerase chain reaction (PCR), nested PCR, semi-nested PCR, Single-Strand Conformation Polymorphism analysis (SSCP), ligase chain reaction (LCR) and strand displacement amplification (SDA). Detection of transrenal DNAs is also performed through hybridization of at least one labeled probe.

The amplification and detection of urinary nucleic acids from non-viral pathogens may be used to detect the presence of these pathogens, and thus diagnose the infection of a subject with these pathogens and to diagnose pathologies associated with the infection of a subject by these pathogens. Further, the detection of these pathogens may be used to monitor treatment of the infections and pathologies associated with these pathogens. Also, detection of these pathogens may be used to suggest treatments for a subject in which the pathogens are detected. These treatments may be used to relieve symptoms which are associated with the detection of pathogens or diagnosis with infection of the pathogens.

Non-viral pathogens which are able to be detected by the presence of their nucleic acids in mammalian urine include bacteria and parasites. Bacterial species which are detectable using the compositions and methods of the invention include *Helicobacter pylori* (*H. pylori*), *Mycobacterium tuberculosis* (*M. tuberculosis*, MTB or TB), and *Bacillus anthracis* (*B. anthracis*). Parasite species which are detectable using the compositions and methods of the invention include *Plasmodium* species including *Plasmodium falciparum* and *Leishmania* species.

Detection of the Presence of Pathogenic Microorganisms
Bacteria
*Helicobacter pylori*

Most cases of peptic ulcer disease, gastric mucosa associated lymphoid tissue (MALT) lymphoma and cancer of the distal stomach are complications of *Helicobacter pylori* infection. (Axon A T. Gut. 1999 July; 45 Suppl 1:I1-4). However, most *H. pylori*-positive individuals remain symptom free throughout their life. Symptoms associated with *H. pylori* infection include abdominal discomfort, weight loss, poor appetite, bloating, burping, nausea and vomiting. A widely accepted explanation of this phenomenon is that the outcome of *H. pylori* colonization is determined by combination of several factors including the genotypes of the bacteria and the host and the environmental cofactors such as diet and smoking. For the successful medical management of the infection it is very important the development of diagnostics tools to direct the decision concerning the treatment of the carriers. The test should give information about the genotype of the bacteria in the carrier.

Colonizing human stomach *H. pylori* strains are genetically very diverse. Observed diversity is attributed to both horizontal transfer of genetic material between coexisting strains as well as to the instability of the bacterial genome. Polymorphism occurs due to point mutations, substitutions, insertions, deletions that may involve one or more genes (Akopyanz, N. S., et al. 1992. Nucleic Acids Res. 20:5137-5142; Achtman, M., et al. 1999. Mol. Microbiol. 32:459-470; Tomb, J.-F., et al. 1997. Nature. 388:539-547; Alm, R. A., et al. 1999. Nature. 397:176-180; Kleanthous, H., et al. 1991. Mol. Microbiol. 5:2377-2389; Kersulyte, D., et al. 1998. Gene. 223:175-186.) Therefore, important initial step for the development of genetic test is the selection of specific genetic markers of *H. pylori* associated with clinical symptoms. There are numerous publications concerning the genetic markers associated with elevated virulence of the bacteria and the disease.

A major genetic determinant of *H. pylori* virulence is the cag pathogenicity island (cag PAI) (Blaser, M. J., et al. 1995. Cancer Res. 55:2111-2115; Cover, T. L., et al. 2001. *Helicobacter pylori* pathogenesis. Academic Press, San Diego, Calif.; Mobley, H. L. 1996. Am. J. Med. 100:2S-11S.), a 40-kb region of chromosomal DNA that is present in some *H. pylori* strains but absent from others. The cag PAI encodes a type IV secretion system and an immunodominant antigen, CagA, which is translocated into gastric epithelial cells. In comparison to infection with cag PAI-negative *H. pylori* strains, infection with cag PAI-positive strains is associated with an increased severity of gastric mucosal inflammation, an increased risk for development of peptic ulceration, and an increased risk of gastric cancer (Ho, S. A., et al. 1991. J. Clin. Microbiol. 29:2543-2549). cagA is present in only 60-70% of H pylori isolates in Western countries. Over 80% of patients with ulcers harbor cagA positive strains (Atherton J C. Gut. 1997 June; 40(6):701-3; Tummuru M K R, et al. Infect Immun 1993; 61:1799-809; Atherton J C, et al. Curr Microbiol. 1999 October; 39(4):211-8.).

In contrast to cagA, the gene encoding the vacuolating cytotoxin (vacA) is present in all *H. pylori* strains analyzed so far. But only 50% of them produce an active vacuolating cytotoxin. Production and cytotoxicity of the vacA protein is determined by its structure. There are two polymorphic regions in the vacA gene: the region encoding the signal sequence with two distinct types of s1 and s2, and midregion marked as m1 and m2. Existence of combination of all s and m types was registered except s2/m1. Most active genotype of vacA gene is shown to be s1/m1 followed by s1/m2. Very little activity or no activity was seen for the type s2/m2. Studies in US demonstrated that over 90% of patients with duodenal ulcer disease had vacA s1 strains and those with s2 strains were at the level of uninfected patients. There is very close genetic linkage between cagA and vacA s1/m1 genotypes. In this pair of genetic markers vacA is considered to be surrogate for the cagA (Cover L, T et al. J Biol Chem 1994; 269: 10566-73; Graham D Y, and Yamaoka Y. Disease-specific *Helicobacter pylori* virulence factors: the unfulfilled promise.Helicobacter. 2000; 5 Suppl 1:S3-9; discussion S27-31).

There are many other *H. pylori* genetic markers studied such as: 16S rRNA gene, the random chromosome sequence, the 26-kDa species-specific antigen (SSA) gene, the ureaseA (ureA) gene, and the urease C (ureC) gene (Valentine, J. L., et al. 1991. J. Clin. Microbiol. 29:689-695; Hammer, M., T. et al. 1992. J. Clin. Microbiol. 30:54-58; Clayton, C. L., et al. 1992. J. Clin. Microbiol. 30:192-200; Bickley, J., et al. 1993. J. Med. Microbiol. 39:338-344; Lu J J, et al. J Clin Microbiol. 1999 March; 37(3):772-4.).

Thus, according to the methods and compositions of the invention, and explained in more detail in the Examples below, *H. pylori* presence and virulence can be detected through the isolation and detection of *H. pylori* transrenal-DNA. Methods of detecting the presence and genotype of *H. pylori* in urine have not been shown before.

*Mycobacterium tuberculosis*

Tuberculosis remains the second most common cause of death from an infectious disease in the world in spite of advances in the implementation of control strategies during the last decade (Elzinga G, et al. Lancet 2004; 363:814-9). Symptoms of tuberculosis include cough that is worse in the morning (sometimes with hemoptysis, blood in the sputum), chest pain, breathlessness, night sweats, and signs of pneumonia. In advanced disease, there may be extreme weight loss. However, no highly sensitive molecular-based test for the detection of *M. tuberculosis* has yet been discovered. Effective treatment of active tuberculosis is the cornerstone of tuberculosis control, and it has been shown that a mere 1% increase in the rate of detection of active cases can save thousands of lives and avert thousand of new tuberculosis cases in high incidence countries (Currie C S, et al. AIDS. 2003; 17:2501-8). Consequently, the availability of new diagnostic tools that are more accurate and accessible will greatly benefit individual patients and significantly contribute to the control of the disease.

Advances in knowledge of the genetic structure of tubercle bacillus have recently contributed to the development of several new molecular methods for detection and identification of *Mycobacterium tuberculosis* from cultures or directly from biological specimens (Drobniewski F A, et al. Lancet Infect Dis. 2003; 3:141-7). Molecular diagnostic tests which involve the detection of specific nucleic acid sequences could be used for rapid diagnosis of both pulmonary and extrapulmonary tuberculosis. In pulmonary tuberculosis specificity of diagnostic tests based on direct identification of *M. tuberculosis* in the sputum using PCR generally exceeds 98% and sensitivity is also high in patients whose sputum smear is positive for acid-fast bacilli on microscopic examination. However, the sensitivity of such tests may be less than 50% for patients with negative sputum smear. (Drobniewski F A, et al., Piersimoni C and Scarparo C. J Clin Microbiol. 2003; 41:5355-65; Sarmiento O L, et al. J Clin Microbiol. 2003; 41:3233-40). The presence of DNA fragments derived from *M. tuberculosis* have been shown before, but only when the pathogen itself was present in the urine. (Del Portillo et al. J. Clin. Microbiol., 29(10):2163-2168 (1991); Kolk et al. J. Clin. Microbiol., 30(10):2567-2575 (1992); Kox et al. Neurology, 45(12):2228-2232 (1995) and Zambardi et al. Mol. Cell. Probes, 9:91-99 (1995)).

The present invention allows for the detection of *M. tuberculosis* through identifying its transrenal DNA in the urine of patients with pulmonary tuberculosis. This approach is more attractive than tests using sputum samples because urine specimens are easier and safer to collect than sputum which can generate infectious aerosols and prove to be difficult to obtain, especially in children.

Despite a previous study suggesting the potential utility of a urine test for *M. tuberculosis* DNA by PCR in HIV infected patients with pulmonary tuberculosis (Aceti A, et al. Thorax. 1999; 54:145-6), subsequent prospective studies conducted on HIV infected and uninfected patients with pulmonary tuberculosis, resulted in only a 40 to 60% sensitivity. This is too low a sensitivity to support the use of a diagnostic test in clinical practice. In these and other such studies, target urinary DNA was of relatively high molecular weight, amplicon sizes of >500 bp having been employed in the PCR reactions. (Kafwabulula M, et al. Int J Tuberc Lung Dis. 2002; 6:732-7; Torrea G, et al. J Med Microbiol. 2005; 54:39-44).

Previously reported PCR based tests have been used successfully to detect *M. tuberculosis* in the urine of patients with genitourinary tuberculosis (van Vollenhoven P, et al. Urol Res. 1996; 24(2):107-11; Hemal A K, et al. Urology. 2000 Oct. 1; 56(4):570-4; Moussa O M, et al. J Urol 2000; 164: 584-8) in which cases the infectious bacteria are present in the urinary tract. Among these patients, high sensitivity and specificity has been achieved by amplifying large (245 to 1000 bp) fragments of mycobacterial DNA purified from urine sediment and the results of molecular test are strongly correlated with the presence of viable mycobacteria which can be cultured from the urine. Thus, presence of specific DNA fragments in these patients appears to reflect urinary excretion of mycobacteria actively replicating in the urogenital tract.

In contrast, we have discovered that small cell-free *M. tuberculosis* DNA fragments originating from sites of infection outside the urogenital tract are present in the urine in this previously unrecognized range of molecular sizes of less than approximately 200 bp. *M. tuberculosis* specific DNA sequences can be easily detected as short fragments of less than 200 bp in the soluble fraction of urine specimens from patients with pulmonary tuberculosis. These specific DNA fragments disappear following successful tuberculosis treatment. This is demonstrated in more detail in the Examples below.

The data on *M. tuberculosis* Tr-DNA disappearance during the course of treatment supports the potential utility of this test in monitoring the clinical course of the disease. It is also clear that small urine specimens can be obtained in the field more easily and safely which is important when broad screening of large populations is of concern to public health. It is also likely that Tr-DNA testing for diagnosis of tuberculosis would have particular value for clinics located in regions having limited resources. Although PCR is currently the preferred method for detecting specific nucleic acid sequences, new emerging technologies can be expected to eventually provide the tools to perform the relatively simple Tr-DNA test in the field (Storhoff J. J., et al. (2004) Biosensors & Bioelectronics 19:875-883; Nam J. M., et al. (2002) J. Am. Chem. Soc 124:3820-3821; Ho H A, et al. (2005) J Am Chem Soc. 127:12673-12676) offering practical advantages over those of PCR can be readily applied to the Tr-DNA test. All steps of the diagnostic process, from Tr-DNA purification to biomarker detection, can be automated and brought to the point of care in small hospitals or even in the field with greater facility than can be done with conventional microbiological testing.

Bacillus anthracis

*Bacillus anthracis* is a spore-forming gram-positive bacterium well known for its recent use as a bioterrorist agent. *Bacillus anthracis* is a large, Gram-positive, spore forming rod shaped bacterium, 1-1.2 µm in width×3-5 µm in length. The bacterium grows in most media under aerobic or anaerobic conditions. *Bacillus anthracis* infection can cause anthrax. Until recently, anthrax was primarily associated with contact with domestic animals. However, more recently *Bacillus anthracis* has been associated with weaponized forms used in terrorism. In the United States, the incidence of naturally-acquired anthrax is extremely rare (1-2 cases of cutaneous disease per year). However, in fall 2001, 22 cases of anthrax (11 inhalation cases, 11 cutaneous cases) were identified in the United States following intentional contamination of the mail.

The most common form of the disease in humans is cutaneous anthrax, which is usually acquired via injured skin or mucous membranes. A minor scratch or abrasion of the skin is contacted by *Bacillus anthracis* spores. The spores germinate, vegetative cells replicate, and an edema develops at the site. This develops into papule within 12-36 hours which changes rapidly to a vesicle, then a pustule (malignant pustule), and finally into a necrotic ulcer from which infection may disseminate, giving rise to septicemia. Lymphatic swelling also occurs and in severe cases, where the blood stream is eventually invaded, the disease is frequently fatal.

Another form of the disease, inhalation anthrax-(woolsorters' disease), results from the inhalation of spore-containing dust. The disease begins with a high fever and chest pain and progresses to a systemic hemorrhagic pathology. It is often fatal if treatment cannot stop the invasive aspect of the infection.

The virulence of *B. anthracis* has been linked to two plasmids, pXO1 and pXO2 (Tumbull, P. C. B., and J. M. Kramer. 1995. Bacillus, p. 349-356. In P. R. Murray, E. J. Baron, et al. (ed.), Manual of clinical microbiology, 6th ed. ASM Press, Washington, D.C.). Isolated Strains lacking pX01 and/or pX02 plasmid were shown to be non-virulent (Mikesell, P., et al. 2002. Plasmids, Pasteur, and anthrax. ASM News 49:320-322. Welkos, S. L. 1991. Microb. Pathog. 10:183-198.).

The plasmid pXO1 (110-MDa) carries three anthrax toxin proteins coding genes, edema factor (cya), lethal factor (lef), and protective antigen (pag) (Uchida, I., K. et al. 1986. J. Gen. Microbiol. 132(Pt. 2):557-559.). Products of these genes act in paired combinations to produce the two anthrax toxins: edema toxin (pag and cya) and lethal toxin (pag and lef) (Leppla, S. H. 1995. Bacterial toxins and virulence factors in disease, p.543-572. Marcel Dekker, New York, N.Y.). These toxicity loci on pXO1 are commonly used as specific genetic markers for PCR detection of *B. anthracis*. Chromosomal genetic markers such as rpoB, gyrA, rRNA were also successfully utilized for the same purposes.(Fasanella, A., S. et al. 2001. Vaccine 19:4214-4218., Qi, Y., et al. 2001. Appl. Environ. Microbiol. 67:3720-3727., Ramisse, V., et al. 1996. FEMS Microbiol. Lett. 145:9-16. Oggioni M R, et al. 2002 J Clin Microbiol. 40(11):3956-63.) Blackwood K S, et al. 2004 J Clin Microbiol. April; 42(4):1626-30; Drago, L., et al. 2002. J. Clin. Microbiol. 40:4399. Hurtle, W., et al. 2004. J. Clin. Microbiol. 42:179-185.)

Identification of *B. anthracis* can be done clinically by Gram stain, colony morphology, and various biochemical tests (Logan, N. A., and P. C. B. Turnbull. 2004. *Bacillus* and other aerobic endospore-forming bacteria, p. 445-460. In P. R. Murray, et al. (ed.), Manual of clinical microbiology, 8th ed. American Society for Microbiology, Washington, D.C.). However, these methods are time-consuming, therefore more rapid tests, such as PCR, have been developed to detect *B. anthracis* in clinical samples (Oggioni, M. R., et al. 2002. J. Clin. Microbiol. 40:3956-3963.). PCR assays have been widely used to identify *B. anthracis* on the basis of genes associated with pXO1 and pXO2 plasmids. (Higgins, J. A., et al. 2003. Appl. Environ. Microbiol. 69:593-599. Oggioni, M. R., F. et al. 2002. J. Clin. Microbiol. 40:3956-3963., Patra, G., et al. 2002. Ann. N. Y. Acad. Sci. 969:106-111.)

However, previous tests used samples isolated from nasal passages. These samples may potentially contain infective pathogen, while urine samples do not. The methods and compositions of the invention are used to detect the presence of *B. anthracis* in subjects through identification of transrenal DNA from *B. anthracis* in the urine of the subjects. These compositions and methods are described in more detail in the Examples below.

Parasites

*Plasmodium* species

It is estimated that there are at least 300 million acute cases of malaria each year globally, resulting in 1.5 to 2.7 million deaths. About 90% of these deaths occur in Africa, mostly in young children. According to the U.S. Centers for Disease Control and Prevention, more than 1000 new cases are reported annually in U.S. travelers returning from malaria-endemic areas. Symptoms of malaria include chills, fever, anemia and jaundice.

Four species of malaria parasites can infect humans under natural conditions: *Plasmodium falciparum, P. vivax, P. ovale* and *P. malariae*. The first two species cause the most infections worldwide. *Plasmodium falciparum* is the agent of severe, potentially fatal malaria, causing an estimated 700,000-2.7 million deaths annually, most of them in young children in Africa. *Plasmodium vivax* and *P. ovale* have dormant liver stage parasites ("hypnozoites") which can reactivate ("relapse") and cause malaria several months or years after the infecting mosquito bite. *Plasmodium malariae* produces long-lasting infections and if left untreated can persist asymptomatically in the human host for years, even a lifetime.

Molecular diagnostic methods have been developed based on the detection of the nucleic acids of the pathogenic agent in the blood or plasma samples, or in the cell cultures, taken from the patient. These assays are generally much more sensitive than the immunological assays. However, they may require the presence of special equipment and qualified personnel. Furthermore, the biological samples—in the case of plasma, blood, or cell cultures—are difficult to store unaltered, except under controlled temperature conditions. For example, methods for the detection of *Plasmodium* in blood have been reported by Gal S., et al. (2001), *Ann N Y Acad Sci.* 945: 234-238.

The present invention provides compositions and methods for the detection of *Plasmodium* species, potentially very soon after infection, by isolating and detecting *Plasmodium* species transrenal DNA in subjects. A more detailed description of these compositions and methods are found below in the Examples.

*Leishmania* Species

About 12 million people throughout the world suffer from leishmaniasis. The disease threatens populations of 30 million people in 88 countries. Over the last 10 years endemic regions have been growing, with a sharp increase in the number of recorded cases of the disease. In addition, as a result of epidemiological changes, leishmaniasis is sharply increasing in populations which are also threatened by overlapping AIDS infection. Molecular diagnostic methods have been developed based on the detection of the nucleic acids of the pathogenic agent in the blood or plasma samples, or in the cell cultures, taken from the patient. These assays are generally much more sensitive than the immunological assays. However, they may require the presence of special equipment and qualified personnel. Furthermore, the biological samples—in the case of plasma, blood, or cell cultures—are difficult to store unaltered, except under controlled temperature conditions. For example, methods for the detection of *Leishmania* in blood have been reported by Disch J, et al. *Acta Trop.* 2004 November-December; 92(3):279-83; Disch J, et al., *Trans R Soc Trop Med Hyg.* 2003 July-August; 97(4):391-5; and Lee N, et al., *Cell Death Differ.* 2002 January; 9(1):53-64. The symptoms of *leishmaniasis* include fever, fatigue, weakness, appetite loss, weight loss, abdominal discomfort, vomiting, diarrhea, cough, scaly skin, thinning hair, macule or papule forming on the skin, skin ulcer, nasal stuffiness, nosebleed, difficulty swallowing and difficulty breathing.

The present invention provides compositions and methods for the detection of *Leishmania* species, potentially very soon after infection, by isolating and detecting *Leishmania* species transrenal DNA in subjects. A more detailed description of these compositions and methods are found below in the Examples.

Urinary Nucleic Acids in Non-viral Pathogen Infections

The present invention describes a method for diagnosing and/or monitoring of a non-viral pathogen infection by detecting and quantification of the nucleic acids of pathogenic agents in urine. It has been discovered that the nucleic acids of these pathogenic agents are detectable in urine. Many of these pathogen specific nucleic acids cross the transrenal barrier (Tr-NA) and can be detected in urine as low-molecular-weight fragments (which tend to be shorter than 1,000 bp in length, but are preferably less than 500 bp in length, and more preferably shorter than 250-300 bp in length or shorter than 250 bp in length) through molecular methods known in the art. Other pathogen specific nucleic acids may be shed by cells that are within the kidney, and thus do not have to cross the transrenal barrier in order to be detected in the urine. Further, some pathogen specific nucleic acids may be found in the urine through other mechanisms besides crossing the transrenal barrier or being generated by cells in the kidney.

The presence of transrenal nucleic acids in the case of infections caused by pathogenic agents according to the present invention also relates to infections that do not directly involve the urinary tract, even in the absence of hematuria or of pathologies that lead to the rupture, or that alter the normal integrity, of the renal barrier. Transrenal nucleic acids are nucleic acids that have crossed the kidney barrier. Generally, the transrenal nucleic acids (Tr-NA) according to the invention are not associated with, and are not derived from, the DNA of cells that are lost or released in the urinary tract. Instead, the transrenal nucleic acids that are detected in the present invention generally have crossed the kidney barrier as a cell-free material. Thus, their lengths are smaller than about 1000 base pairs, e.g., smaller than about 500, smaller than about 300, smaller than about 250, or between about 100 and about 200 bases or base pairs, as opposed to other cases in which DNA usually has a longer length, greater than 1000 bases or base pairs. In embodiments, the Tr-NAs are DNA fragments.

The discovery confirms the presence of urinary nucleic acids or transrenal nucleic acids derived from pathogenic bacteria and parasites in urine, and therefore is applicable to the diagnosis of all infectious diseases caused by non-viral pathogens.

In one embodiment, the invention relates to a method for the diagnosis a non-viral pathogenic infection in a subject by detection of pathogen-related transrenal nucleic acids in a urine sample from the subject. In some embodiments, the invention further includes the step of quantifying the pathogen-related transrenal nucleic acids. In other embodiments, the invention provides for methods of monitoring a parasite infection by repeated detection of pathogen-related transrenal nucleic acids in a subject over a period of time.

In one embodiment, the invention relates to a method for diagnosis of an infection in a subject, including the step of detection of the presence pathogen-related transrenal nucleic-acid sequences in a urine sample of the subject. In a further embodiment, the invention relates to the above method in which the transrenal nucleic acids are isolated from the urine sample prior to detecting the nucleic acids.

In another embodiment, the method according to the invention may include an initial treatment of the urine sample prior to detection. In a specific embodiment, the invention includes the pretreatment of the urine sample with agents that inhibit the degradation of the nucleic acids. Included are the enzymatic inhibitors, such as chelating agents, detergents, or denaturing agents, and preferably DNase or RNase inhibitors, which include EDTA, guanidine HCl, guanidine isothiocyanate, N-lauryl sarcosine, and sodium dodecyl sulfate.

According to another embodiment, the urine sample may be centrifuged (at a speed between 3000 g and 5000 g, such as between 3500 g and 4500 g) or filtered in order to separate the fraction consisting of cells and their fragments from the supernatant containing the soluble DNA or RNA and their proteinous complexes. However, the urine sample may also be subjected to nucleic acid detection procedures without this fractionation.

The optional isolation or purification and quantification of the transrenal nucleic acids are achieved through the use of chemical or physical methods that are already known in the art. It includes at least one purification step, using methods selected from among extraction with organic solvents, filtration, precipitation, absorption on solid matrices (e.g., via ion exchange), affinity chromatography or else molecular exclusion chromatography or combinations of these methods.

However, the purification method must be appropriate for the isolation of DNA (single- or double-helix) that are less than 1000 nucleotides in length, with a corresponding molecular weight, assuming, as the average molecular weight, that of a nucleotide having a value of 330 Daltons. In some embodiments, the purification is specific for fragments that are smaller than 500 nucleotides (nt) in length, with a corresponding molecular weight, such as fragments whose lengths are less than 300 nt, fragments less than 250 nt in length, or fragments whose lengths are between 100 and 200 base pairs of nucleic acids (nt).

In an embodiment, the DNA isolation method is implemented by pretreating the urine sample with a denaturing agent, such as urea, guanidine HCl, or guanidine isothiocyanate. The sample is then caused to pass through a solid phase, such as a matrix consisting of a silica-based resin which, in the presence of chaotropic salts, such as guanidine isothiocyanate, binds the nucleic acids. Even more preferably, a resin such as Wizard Purification Resin® (Promega®) is utilized. The sample is then collected by elution in a buffer, such as Tris-EDTA (Tris 1-10 mM, EDTA 1-10 mM), or in water.

In a preferred embodiment, the characterization and the determination of the presence of DNA of the pathogenic agent is performed through a technique selected from the group consisting of: hybridization of the nucleic acids, a cycling probe reaction (F. Bekkaoui et al., in *BioTechniques* 20:240-248 [1996]), a polymerase chain reaction (*PCR Protocols: A Guide to Methods and Applications*, by M. Innis et al.; Elsevier Publications, 1990), a nested polymerase chain reaction, single-strand conformation polymorphism, or ligase chain reaction (LCR) (F. Barany, in *PNAS USA*, 88:189-93 [1991]), strand displacement amplification (SDA) (G. K. Terrance Walker, et al., in *Nucleic Acid Res*, 22:2670-77 [1994], and restriction fragments length polymorphism. Polymerase chain reaction (PCR) is the preferred method for the detection or analysis of nucleic acids. More preferred is dual-amplification PCR, with the use of a nested primer in nested or semi-nested PCR (reference: bio.davidson.edu/courses/genomics/method/NestedPCR.html).

Methods for the Amplification and Detection of Urinary Nucleic Acids

The term nucleic acid refers to an oligonucleotide, nucleotide, polynucleotide, or fragments/parts thereof and to DNA or RNA of natural (e.g., genomic) or synthetic origin. It may have a double or single helix, and may also represent the sense or antisense direction of a sequence. Parallel helix (5'→3'); antiparallel helix (3'→5'). The terms oligonucleotide, polynucleotide and nucleic-acid polymer are equivalent, and are understood as referring to a molecule consisting of more than two deoxyribonucleic or ribonucleic acid bases. The number of nucleotides (bases) and the length of the oligonucleotide fragment may vary. They may be synthesized in different ways. The sequences are traditionally defined as starting with 5' and ending with a 3'. These numbers indicate the direction of the sequence.

DNA isolated from the urine of a subject may then be amplified in order to be detected. Amplification methods include polymerase chain reaction (PCR), nested PCR, semi-nested PCR, Single-Strand Conformation Polymorphism analysis (SSCP), ligase chain reaction (LCR) and strand displacement amplification (SDA). Detection of transrenal DNAs is also performed through hybridization of at least one labeled primer.

Hybridization is a method that allows two nucleic-acid sequences to recognize each other as complementary and to join together (annealing). Complementarity/Complementary sequences are sequences of polynucleotides that interact with each other, depending on the interaction between the bases. For example, the AGTC sequence is complementary to TCAG according to standard Watson Crick base pairing. However, other combinations such as Hoogstein base pairing are well known to those having ordinary skill in the art. It is possible to have a fully or partially complementary sequence, and this is what determines the efficiency or attractive force between the two sequences. Average complementarity would prevent a strong complementarity from hybridizing, under conditions that would allow it to remain attached.

The ability of nucleic sequences to hybridize is a well-known phenomenon. The first hybridization method was described in Marmur & Lane, *PNAS USA*, 46:453 (1960) and 461 (1960), but since then has been perfected as a technique in molecular biology. Today, the term "hybridization" includes, among others, slot/dot and blot hybridization. The conditions that allow nucleotide sequences to recognize each other (hybridization) can be modified in such a way as to produce complete hybridization (complementarity with high specificity) or partial hybridization (complementarity with average specificity). In the present application, whenever the term "hybridization" is used, the conditions should be understood as referring to those that allow average or high complementarity. The technician in the field can calculate how many artificial sequences are needed to encourage hybridization between two complementary sequences in the opposite direction, known as antiparallel association.

A probe is an oligonucleotide that can be produced artificially or naturally, and that forms a combination with another nucleic-acid sequence. The probes are useful in discovering specific sequences in a sample containing unknown DNA. In this patent, all of the probes can be bound to a signaling molecule (or reporter). The reporter molecule makes it possible to detect the probe (for example, through enzymatic reactions (e.g., ELISA (Enzyme-Linked Immunosorbent Assay)), radioactivity, fluorescence, or other systems).

Polymerase chain reaction (PCR) is a method of amplification of a DNA sequence using complementary primers and a heat sensitive polymerase. One class of enzymes utilized in the amplification of specific nucleic acids are DNA polymerases referred to as Taq (*Thermus aquaticus*) polymerases. Primers are oligonucleotides from which, under proper conditions, the synthesis of a polynucleotide sequence can be initiated. A primer may exist naturally (for example, in an enzymatic digestion of a polynucleotide), or may be obtained through chemical synthesis. The product amplified in PCR is often referred to as an amplicon.

Nested PCR is a second PCR which is performed on the product of an earlier PCR using a second set of primers which are internal to the first set of primers, referred to as nested primers. This significantly improves the sensitivity and specificity of the PCR. Nested primers are primers internal to an amplicon obtained with a first PCR cycle. The amplification process that uses at least one nested primer improves specificity, because the non-specific products of the first cycle are not amplified in the second cycle, because they lack the sequence that corresponds to the nested primer. Semi-nested PCR is a second PCR which uses one new primer and one of the original primers. This process also improves specificity.

Ligase Chain Reaction (LCR) is a method of DNA amplification similar to PCR. LCR differs from PCR because it amplifies the probe molecule rather than producing an amplicon through polymerization of nucleotides. Two probes are used per each DNA strand and are ligated together to form a single probe. LCR uses both a DNA polymerase enzyme and a DNA ligase enzyme to drive the reaction. Like PCR, LCR requires a thermal cycler to drive the reaction and each cycle results in a doubling of the target nucleic acid molecule. LCR can have greater specificity than PCR.

In Single-Strand Conformation Polymorphism (SSCP) analysis a small PCR product (amplicon) is denatured and electrophoresed through a non-denaturing polyacrylamide gel. Thus, as the PCR product moves into and through the gel (and away from the denaturant), it will regain secondary structure that is sequence dependent (similar to RNA secondary structure). The mobility of the single-stranded PCR products will depend upon their secondary structure. Therefore, PCR products that contain substitutional sequence differences as well as insertions and deletions will have different mobilities.

Strand displacement amplification (SDA) is an isothermal nucleic acid amplification method based on the primer-directed nicking activity of a restriction enzyme and the strand displacement activity of an exonuclease-deficient polymerase.

The terms purification or isolation refers to a process for removing contaminants from a sample, where the result is a sample containing 50%, 60%, 75%, 90% or over 90% of the material toward which the purification procedure is directed.

For stringent temperature conditions in the case of nucleic-acid hybridization, these terms usually refer to a variable temperature between a maximum, for a nucleic acid, represented by Tm less 5° C., and a minimum represented by Tm less 25° C. The technique used in the field utilizes stringent temperature conditions, in combination with other parameters (e.g., saline concentration), to distinguish sequences with a quasi-exact homology.

Stringent conditions are known to those skilled in the art and can be found in Ausubel, et al., (eds.), CURRENT PROTOCOLS IN MOLECULAR BIOLOGY, John Wiley & Sons, N.Y. (1989), 6.3.1-6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions are hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2×SSC, 0.01% BSA at 50° C.

In a second embodiment, a nucleic acid sequence that is hybridizable to the nucleic acid molecule comprising the nucleotide sequence, or fragments, analogs or derivatives thereof, under conditions of moderate stringency is provided. A non-limiting example of moderate stringency hybridization conditions are hybridization in 6×SSC, 5× Reinhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well-known within the art. See, e.g., Ausubel, et al. (eds.), 1993, CURRENT PROTOCOLS IN MOLECULAR BIOLOGY, John Wiley & Sons, NY, and Krieger, 1990; Gene TRANSFER AND EXPRESSION, A LABORATORY MANUAL, Stockton Press, NY.

In a third embodiment, a nucleic acid that is hybridizable to the nucleic acid molecule, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel, et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo and Weinberg, 1981. *Proc Natl Acad Sci USA* 78: 6789-6792.

The invention also provides a kit for detecting and/or genotyping *Helicobacter pylori* in a urine sample from a subject in need thereof, comprising at least one forward primer selected from SEQ ID NOs: 5, 8, 10, 11, 12 and 15 and at least one reverse primer selected from SEQ ID NOs: 6, 7, 9, 13, 14, 16 and 17, either in the same or separate packaging, and instructions for its use.

The invention also provides a kit for detecting and/or genotyping *Mycobacterium tuberculosis* in a urine sample from a subject in need thereof, comprising at least one forward primer selected from SEQ ID NOs: 34, 37 and 39 and at least one reverse primer selected from SEQ ID NOs: 35, 36, 38 and 40, either in the same or separate packaging, and instructions for its use.

The invention also provides a kit for detecting and/or genotyping *Bacillus anthracis* in a urine sample from a subject in need thereof, comprising at least one forward primer selected from SEQ ID NOs: 41, 43, 45, 47, 48 and 50 and at least one reverse primer selected from SEQ ID NOs: 42, 44, 46 and 49, either in the same or separate packaging, and instructions for its use.

The invention also provides a kit for detecting and/or genotyping *Plasmodium* species in a urine sample from a subject in need thereof, comprising at least one forward primer selected from SEQ ID NOs: 18, 21 and 23 and at least one reverse primer selected from SEQ ID NOs: 19, 20 and 22, either in the same or separate packaging, and instructions for its use.

The invention also provides a kit for detecting and/or genotyping *Leishmania* species in a urine sample from a subject in need thereof, comprising at least one forward primer selected from SEQ ID NOs: 26, 28, 30, 32 and 51 and at least one reverse primer selected from SEQ ID NOs: 24, 25, 27, 29, 31 and 33, either in the same or separate packaging, and instructions for its use.

The invention will be further described in the following examples, which do not limit the scope of the invention described in the claims.

EXAMPLES

All of the methodology described herein may be modified by the technician in the field with no change in the basic principal idea.

Example 1

Stabilization and Preparation of the Samples

All of the steps of the preparation of the urine samples and of the analysis of the transrenal DNA were performed at room temperature. Briefly, approximately 50-60 ml of urine samples were collected from each patient participating in the study. Within 30 minutes after collection, a solution consisting of 0.5M EDTA and 0.5M Tris-HCl, at a pH ranging from 8.0 to 8.5, was added at a final concentration of 10 mM in order to inhibit the nucleases that might be present in urine samples. At least three nucleolytic enzymes were identified in urine, DNase I, DNase II and phosphodiesterase. EDTA inhibits the activity of DNase I and phosphodiesterase by chelating divalent metals such as $Mg^{2+}$, $Ca^{2+}$ and/or others that are required for their activity. DNase II is maximally active in acidic environment. Supplementing the urine with Tris-HCl pH 8.0 buffer increases the pH of urine thereby inhibiting the activity of DNase II.

The stabilized urine samples can be stored, in aliquots of 5 ml, at −80° C. Optionally, 25 mL of saline solution is frozen to act as a control.

Other methods for the preparation of urine samples and for the extraction of the DNA are described in PCT patent No. WO 98/54364, which is incorporated by reference in its entirety.

Example 2

Urine Fractionation

For Tr-DNA based applications, that involve quantitative Tr-DNA analysis, urine fractionation is often required. It reduces the impact of nucleoproteins from cells present in urine on accurate quantitation of Tr-DNA/protein complex, total Tr-DNA, or specific genetic markers. In our experiments we have employed two procedures for urine fractionation, centrifugation and filtration. Both were carried out immediately after urine collection and, before supplementing the specimen with EDTA-Tris stabilizing mixture. Urine may be kept in this condition as long as urine cells are intact and their constituents do not leak into urine and contaminate Tr-DNA by cellular DNA.

For filtration one can use filters with pore size ranging from 0.1 to 5 µm with reduced nucleic acid and protein binding capacity. The choice of the filter depends on target under analysis. For bacterial pathogens smaller pores are required. In our experiments we used luer-lock 0.45 µm Filter Units (Cat. No. SLHV033RS) or 0.45 µm 150 ml Filter Unit STERICAP (Cat. No. SCHVU01RE) both from Millipore. After filtration the samples were supplemented with EDTA-Tris conservation solution and taken into downstream processes of DNA extraction or aliquoted and stored frozen at −80° C. Urine cellular fraction can be harvested by extracting it from the filter by applying a solution (high concentrations of salts or chaotropic agents) that is known to dissolve cells.

Urine fractionation by centrifugation in our experiments was carried immediately after sample collection, before addition of preservation mixture. Centrifugation was performed at room temperature at RCF ranging between 3500 and 4000× g for approximately 15 min. Supernatant was carefully collected and manipulated per the procedure described above for urine filtration. The pellet consisting mainly of cells and cellular debris was resuspended in physiological solution and stored at −80° C.

Example 3

Extraction and Purification of the Nucleic Acids from Urine

In our experiment we used silica based DNA extraction protocol in two different formats. One was vacuum driven and the second, centrifugation.

Vacuum Based Procedure

To the urine sample 6 M Guanidine Thiocyanate (GITC) (AMRESCO, Cat. No.0380) was added to final concentration not less than 3 M. This solution was mixed vigorously and supplemented with 0.25 ml of Wizard silica suspension (PROMEGA, Cat. No. A7141) per 10 ml of initial urine volume. To capture DNA the mixture was continuously rotated for 1 hour at room temperature. Resin with captured DNA was collected by loading the mixture on a minicolumn (PROMEGA, Cat. No. A7211) syringe assembly attached to a vacuum line. Resin was collected by applying vacuum, washed twice with 5 ml of 3M GITC solution. The resin was further washed twice by a solution consisting of 80% ethanol and 50 mM NaCl. Then the minicolumn was detached and the resin was additionally washed twice with 96% ethanol by centrifugation on a benchtop microcentrifuge in 1.5 ml tubes. DNA was eluted by brief centrifugation with hot water in a volume of not more than 1/20 of urine initial volume.

Centrifugation Based Procedure

To the urine sample 6 M Guanidine Thiocyanate (GITC) (AMRESCO, Cat. No.0380) was added to final concentration not less than 3 M. This solution was mixed vigorously and supplemented with 0.25 ml of Wizard silica suspension (PROMEGA, Cat. No. A7141) per 10 ml of initial urine volume. To capture the DNA, the mixture was continuously rotated for 1 hour at room temperature. Resin with captured DNA was collected by centrifugation at approximately 4000×g for about 5 min at room temperature. Pelleted resin was washed once with GITC solution and once with wash buffer, then was transferred into a mini-column and washed one additional time with 96% ethanol. DNA was eluted with hot water into a microcentrifuge tube by brief centrifugation. DNA was eluted by brief centrifugation with hot water in a volume of not more than 1/20 of urine initial volume.

Example 4

Monitoring of the Integrity of DNA Extraction Procedure

The DNA extraction procedure was routinely monitored by testing the purified DNA for the presence of selected control DNA sequences. For the purposes of detection of Tr-DNA of infectious agents the integrity of DNA purification procedure was monitored using beta-actin and beta-globin as markers for human and rabbit urine, respectively. PCR amplification of above targets is a surrogate for the estimation of DNA yield and quality. Primer pairs used in these studies are presented in Table 1.

TABLE 1

| ID | Sequence | Pr. Length (nt) | Tm | Amp. Size (bp) | SEQ ID NO: |
|---|---|---|---|---|---|
| ES0007 | AAGACAGTGTTGTGGGTGTAGG | 22 | 59.0 | 77 | 1 |
| ES0008 | TCCAAGGCCGCTTTACAC | 18 | 59.8 |  | 2 |
| LEBG_F | GGCACAGGTTTCATCCATTC | 20 | 54.1 | 70 | 3 |
| LEBG_R | GATAGGTCTCTCTTTATGTCTTCAG | 25 | 54.4 |  | 4 |

Figure 2:
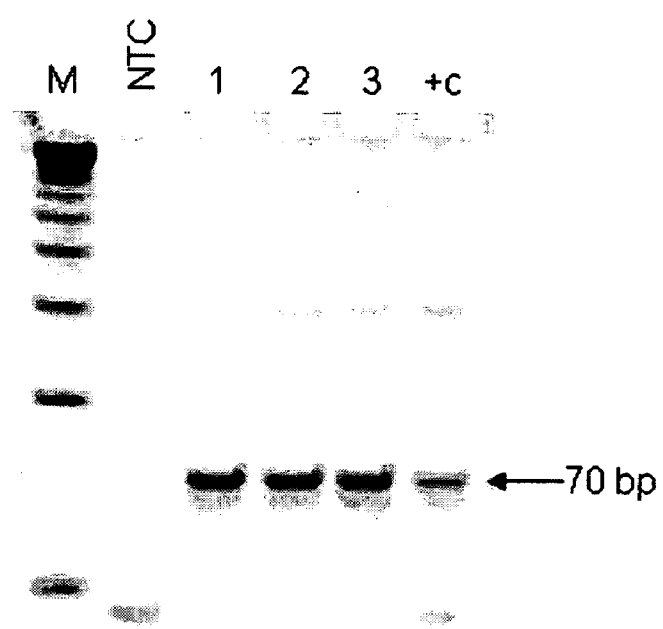
FIG. 2 is a photograph of PCR reactions performed on rabbit urine with primers specifc for rabbit b-globin resolved by electrophoresis.

PCR conditions for both targets were identical. Amplification of isolated DNA equivalent to 300 µl of urine was carried out in 25 ll mixture containing 0.2 µmol/liter of primers ES0007 and ES0008 or LEBG_F and LEBG_R for human b-actin or rabbit b-globin, respectively, 200 µmol/liter dNTP each, and 1 U GoTaq Polymerase (Promega). Thermal profile for both types of reactions was: 94° C. for 5 minutes followed by 35 cycles of 94° C. for 30 seconds, 60° C. for 30 seconds, 72° C. for 1 minute, and 1 cycle of 72° C. for 5 minutes. Ten µl the products were resolved by electrophoresis in 7% polyacrylamide gel, and visualized by ethidium bromide staining. FIG. 1 and FIG. 2 depict the results of PCR of DNA purified from human urine and rabbit urine, respectively.

FIG. 1 shows the results of PCR performed to control the integrity of DNA extraction from human urine. Urine samples are from patients attending doctor's office for endogastroscopy for a test for *Helicobacter pylori*. M—DNA molecular weight standards, 50 bp ladder; NTC—no template control; 1—13 urine from patients.

FIG. 2. shows the results of PCR performed to control the integrity of DNA extraction from rabbit urine. Urine samples were harvested from rabbits infected with *Bacillus anthracis* spores. M—DNA molecular weight standards, 50 bp ladder; NTC—no template control; 1—DNA from urine of uninfected rabbit; 2 and 3—urine of infected rabbit collected 6 an 14 hours after infection, respectively; +c—rabbit genomics DNA

Example 5

Design of PCR Primers

As a general rule, primers for the PCR based analysis of Tr-DNA were designed for target amplicons not more than 200 bp in length.

All primers were screened against the complete sequence of human genome.

For primer design FastPCR software was used (www.biocenter.helsinki.fi/bi/bare-1_html/oligos.htm). The critical parameters for primer design were as follows:

Allow 1 mismatch in 5 nucleotides at 3' end.

At least 2 G or C residues at 3' end.

Only one A or T residue at 3' end.

Maximum Tm of 23° C. for 6 nucleotides at 3' end.

Nested primers were designed using Primer 3 package [see Steve Rozen and Helen J. Skaletsky (2000) Primer3 on the WWW for general users and for biologist programmers. In: Krawetz S, Misener S (eds) *Bioinformatics Methods and Protocols: Methods in Molecular Biology*. Humana Press, Totowa, N.J., pp 365-386] and is available online (frodo.w-i.mit.edu/cgi-bin/primer3/primer3_www.cgi). The only parameter specified for the nested primers was the Tm in order to have primers with annealing temperature not less than external primers.

Example 6

Selection of PCR Primer Sets for the Detection of *H. pylori* Gene Sequences for PCR PCR primers were designed based on consensus DNA sequences created by alignment of corresponding genetic markers nucleotide sequences. DNA sequences of target genes were extracted from GeneBank at NCBI and aligned using BioEdit package (IBIS Therapeutics, Carlsbad, Calif.). Primers are listed in Table 2. For the purposes of present invention two sets of genetic markers were selected: ureA as specie specific marker and cagA as a marker of virulence.

TABLE 2

| ID | Primer Sequence | Amplicon | Nested Amplicon | SEQ ID NO: |
|---|---|---|---|---|
| cagA-f | TCRGAAATTTGGGRMTCAGCGTTAC | 102 bp | 65 bp | 5 |
| cagA-r | TCCATAAAATTTYGGATBBDTYGGGTGTTG | | | 6 |
| cagA-rn | ACGGATCDTTTTGAWGGGACAC | | | 7 |
| vacS1-f | AGCDYCAYACCRCAAVAAAGTCATGCYGC | 104 bp | 71 bp | 8 |
| vacS-r | CTGADACCGTTCCTACAGC | | | 9 |
| vacS-fn | YTTYACRACCGTGATYATTCCAGC | | | 10 |
| vacS2-f | CKCCAAAYGATCCCATACACAGCGAGAG | 109 bp | 71 bp | 11 |
| ureA-f | TGATGGGACYAAACTCGTAACCG | 86 bp | 50 bp | 12 |
| ureA-r | CTTCATTTTTTAAGAACAACTCACCAGGA | | | 13 |
| ureA-nr | ACCATTRGCCTCAATAGGGGTATGC | | | 14 |
| HG16sf | CACTGGGCGTAAAGACYGCGTAG | 113 bp | 63 bp | 15 |
| HG16sr | CCACCTRCCTCTCCCAYACTC | | | 16 |
| HG16snr | GGTTAAGCCATAGGATTTCACAYCTGAC | | | 17 |

Set 1. cagA Gene Primers for Semi-nested-PCR

External Primers:

```
cagA-f:  TCRGAAATTTGGGRMTCAGCGTTAC         (SEQ ID NO: 5)
cagA-r:  TCCATAAAATTTYGGATBBDTYGGGTGTTG    (SEQ ID NO: 6)
```

Product: 102 bp.

Internal Primers:

```
cagA-f:  TCRGAAATTTGGGRMTCAGCGTTAC    (SEQ ID NO: 5)
cagA-rn: ACGGATCDTTTTGAWGGGACAC       (SEQ ID NO: 7)
```

Product: 65 bp.

VacA Region Primers for Semi-nested-PCR,

Set 2. S1 Specific

External Primers

```
vacS1-f  AGCDYCAYACCRCAAVAAAGTCATGCYGC   (SEQ ID NO: 8)
vacS-r   CTGADACCGTTCCTACAGC             (SEQ ID NO: 9)
```

Product 104 bp

Internal Primers

```
vacS-fn  YTTYACRACCGTGATYATTCCAGC   (SEQ ID NO: 10)
vacS-r   CTGADACCGTTCCTACAGC        (SEQ ID NO: 9)
```

Product 71 bp

Set 3. S2 Specific
External Primers vacS2-f  CKCCAAAYGATCCCATACACAGCGAGA  (SEQ ID NO: 11)
         G vacS-r   CTGADACCGTTCCTACAGC          (SEQ ID NO: 9)

Product 109 bp
Internal Primers vacS-fn  YTTYACRACCGTGATYATTCCAGC     (SEQ ID NO: 10)

vacS-r   CTGADACCGTTCCTACAGC          (SEQ ID NO: 9)

Product 71 bp
Set 4. *H. pylori* Specific
External Primers ureA-f   TGATGGGACYAAACTCGTAACCG      (SEQ ID NO: 12)

ureA-r   CTTCATTTTTTAAGAACAACTCACCAGGA (SEQ ID NO: 13)

Product 86 bp
Internal Primers ureA-f   TGATGGGACYAAACTCGTAACCG      (SEQ ID NO: 12)

ureA-nr  ACCATTRGCCTCAATAGGGGTATGC    (SEQ ID NO: 14)

Product 50 bp
Set 5. *Helicobacter* Genus-Specific
External Primers

HG16s-f  CACTGGGCGTAAAGAGYGCGTAG      (SEQ ID NO: 15)

HG16s-r  CCACCTRCCTCTCCCAYACTC        (SEQ ID NO: 16)

Product 113 bp
Internal Primers (i)

HG16s-f  CACTGGGCGTAAAGAGYGCGTAG      (SEQ ID NO: 15)

HG16s-nr GGTTAAGCCATAGGATTTCACAYCTGA  (SEQ ID NO: 17)
         C

Product 63 bp

Example 7

Detection of *H. pylori* in Urine of Patients

Study participants were randomly selected from the patients of the S.Orsola-Malpighi Hospital visiting the Department of Internal Medicine (Bologna, Italy) for routine upper gastrointestinal endoscopy. Infection of these patients was diagnosed by two assay: fast urease test and histological analysis of the biopsy for the presence of bacteria.

Urine specimens were obtained before the endoscopy, and the DNA from whole urine was purified following the protocol described in Examples 1, 2 and 3.

Detection of ureA and cagA specific sequences in urine was carried out by semi-nested PCR. Initial twenty cycles of PCR amplification were performed as following: isolated DNA equivalent to that contained in 5 ml of urine was added to a 25 µl mixture containing 0.2 lmol/liter of outer primers specific for ureA or cagA (SEQ ID NO 12 and 13, or SEQ ID NO 5 and 6, respectively), 5 µl 5×PCR buffer (Promega), 200 µmol/liter dNTP each, and 1 U GoTaq Polymerase (Promega), denatured at 94° C. for 5 minutes followed by 20 cycles of 94° C. for 30 seconds, 62° C. for 30 seconds, 72° C. for 1 minute, and 1 cycle of 72° C. for 5 minutes. One µl of the product from this amplification was diluted 1:10 and 1 µl of the dilution was re-amplified 35 cycles using internal ureA and cagA primers (SEQ ID NO 12 and 13, or SEQ ID NO 5 and 6, respectively), under the same conditions as in the first reaction. The products from the second amplification were resolved by electrophoresis in 7% polyacrylamide gel, and visualized by ethidium bromide staining.

Figure 3:
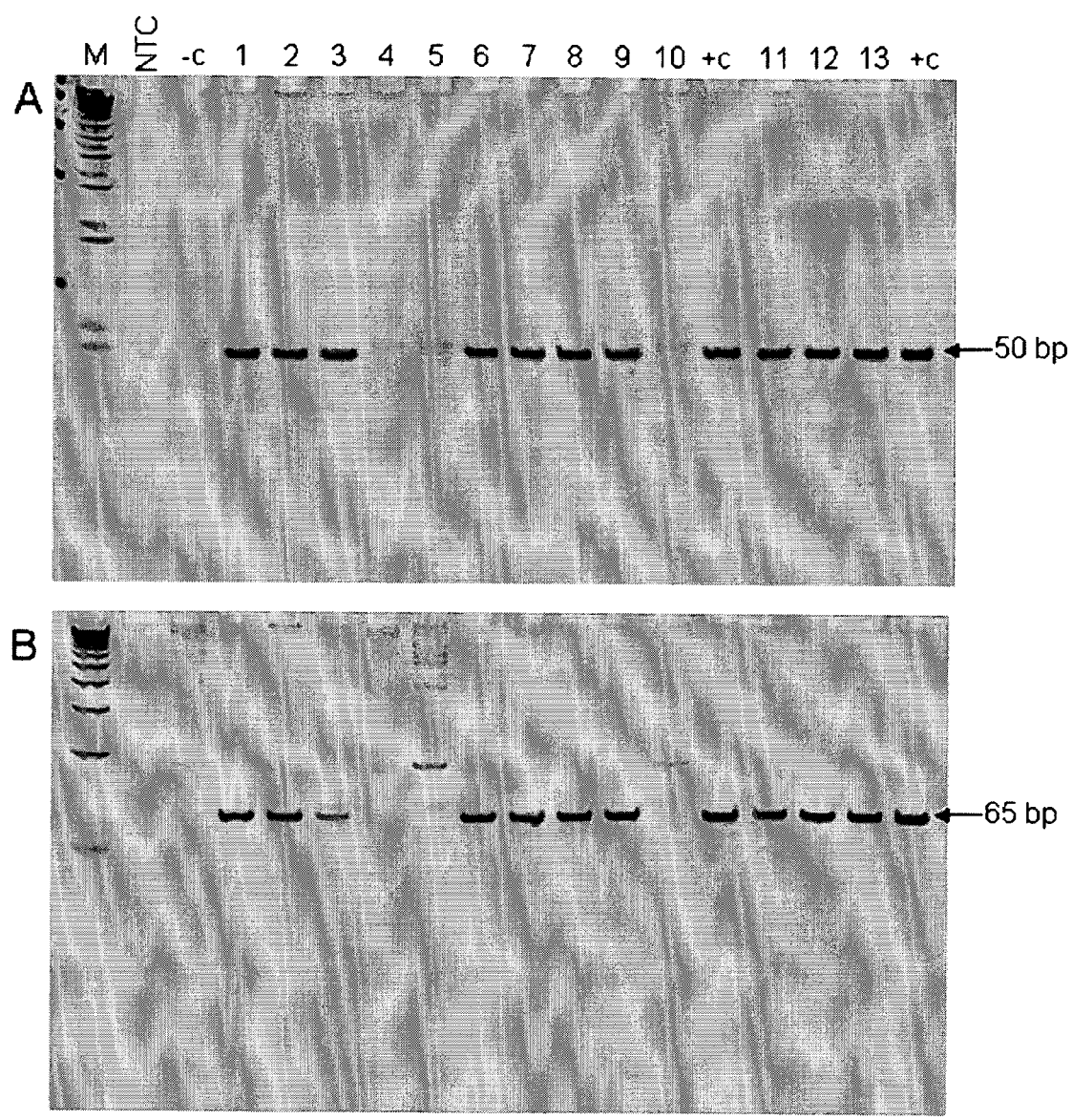
FIG. 3A is a photograph of semi-nested PCR reactions performed on human urine with primers specifc for *H. pylori* ureA sequences resolved by electrophoresis.
FIG. 3B is a photograph of semi-nested PCR reactions performed on human urine with primers specifc for *H. pylori* cagA sequences resolved by electrophoresis.

FIG. 3 shows semi-nested PCR detection of ureA (A) and cagA (B) genes specific DNA sequences in urine of patients (lanes 1-13). NTC—no template control; −c—DNA from the urine of a healthy volunteer; +c—positive control.

Example 8

Selection of PCR Primer Sets for the Detection of *Plasmodium* sp

Primers were designed to detect 18S rRNA genes of all four human pathogenic subtypes *Plasmodium* sp: *P. falciparum; P. vivax; P. malariae*, and *P. ovale* (accession numbers: M19172; X13926; M54897 and L48987, respectively).

PCR primers were designed based on consensus DNA sequences created by alignment of corresponding genes' nucleotide sequences. Nucleotide sequences were aligned using BioEdit package (IBIS Therapeutics, Carlsbad, Calif.). Primers are presented in the Table 3.

TABLE 3

PCR primer pairs for the detection of *Plasmodium* sp.

| Pair No. | Seq Name <ID> | Forward sequence | Seq Name <ID> | Reverse sequence | Product (bp) |
|---|---|---|---|---|---|
| 1 | F-358 <18> | gggtattggccta acatggctatgac | R-405 <19> | aggctccctct ccggaatcg | 67 bp |
| 2 | F-358 <18> | gggtattggccta acatggctatgac | R-456 <20> | agaattgggta atttacgcgcc t | 123 bp |
| 3 | F-1458 <21> | cttgatttcttgg atggtgatgc | R-1526 <22> | ggttaagatct cgttcgttatc gg | 92 bp |
| 4 | F-1385 <23> | cggcttaatttga ctcaacacg | R-1526 <22> | ggttaagatct cgttcgttatc gg | 164 bp |

Example 9

Selection of PCR Primer Sets for the Detection of *Leishmania* sp

For the detection of pathogenic *Leishmania* strains that cause visceral leishmaniasis two sets of primers were designed: first, a set specific for kinetoplast minicircle DNA conserved sequences common for the donovani complex, and a second set specific for 18S rRNA gene common for all *Leishmania* sp.

TABLE 4

PCR primer pairs designed for the detection of Leishmania sp.

| Pair No. | Seq Name <ID> | Forward sequence | Seq Name <ID> | Reverse sequence | Product (bp) |
|---|---|---|---|---|---|
| 1 | F-81 <51> | rggtaggggcgtt ctgc | R-160 <24> | agtttyccgcc ccggag | 101 bp |
| 2 | F-81 <23> | rggtaggggcgtt ctgc | R-156 <25> | cccagtttbcc gccycgga | 97 bp |
| 3 | F-340 <26> | ctattggagatta tggagctgtgc | R-382 <27> | cacacaccgaa ccgargttgc | 64 bp |
| 4 | F-505 <28> | gggagaacgtact ggggcgtc | R-547 <29> | tcgctgtagtt cgtcttggtg | 64 bp |
| 5 | F-37 <30> | ctgttgctgttaa agggttcgtag | R-91 <31> | tccgacatgga cgggacgacc | 76 bp |
| 6 | 13A* <32> | gtgggggaggggc gttct | 13B* <33> | attttacacca accccagtt | 120 bp |

*BELLI A et al. 1998, SIMPLIFIED POLYMERASE CHAIN REACTION DETECTION OF NEW WORLD LEISHMANIA IN CLINICAL SPECIMENS OF CUTANEOUS LEISHMANIASIS, Am. J. Trop. Med. Hyg., 58(1), pp. 102-109

Example 10

Detection of *Plasmodium* Species

Urine sample was taken from a malaria patient infected with *Plasmodium falciparum*. DNA isolated from the whole urine of non-infected patients or from blood of malaria patients was used as negative and positive controls, respectively. For the detection of *Plasmodium* sp specific DNA sequences in urine of a patient semi-nested PCR was performed using two sets of primers targeting two conserved regions of S18 ribosomal RNA gene.

Figure 4:
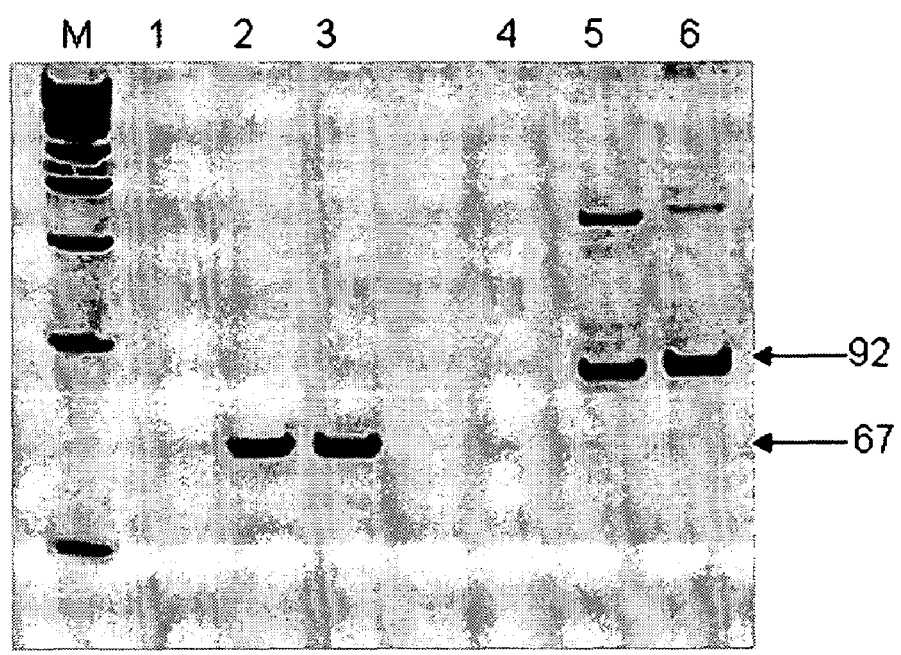
FIG. 4 is a photograph of semi-nested PCR reactions performed on human urine with primers specifc for *Plasmodium falciparum* sequences resolved by electrophoresis.

FIG. 4 illustrates the electrophoresis of the DNA fragments that were amplified via two amplification cycles (semi-nested PCR). Two sets of reactions were carried out:
1. Primer pairs F-358/R-456 for the first PCR and F-358/R-405 for subsequent semi-nested reaction, lanes 1; 2 and 3 are negative control; Tr-DNA from infected patient and DNA extracted from the whole blood of an infected patient, respectively.
2. Primer pairs F-1385/R-1526 for the first PCR and F-1458/R-1526 for subsequent semi-nested reaction, lanes 4; 5 and 6 are negative control; Tr-DNA from infected patient and DNA extracted from the whole blood of an infected patient, respectively.

Lane M—molecular weight standards.
For primer pairs and PCR product sizes see Table 3.

Example 11

Detection of *Leishmaniasis* Species

Urine sample was taken from a *leishmaniasis* patient infected with *Leishmania infantum*. DNA isolated from the whole urine of non-infected patients or from blood of *leishmaniasis* patients was used as negative and positive controls, respectively. For the detection of *Leishmania* sp specific DNA sequences in urine of a patient PCR amplification reaction was carried out using a set of primers specific for kinetoplast minicircle DNA conserved domain (primers 13A/13B).

Figure 5:
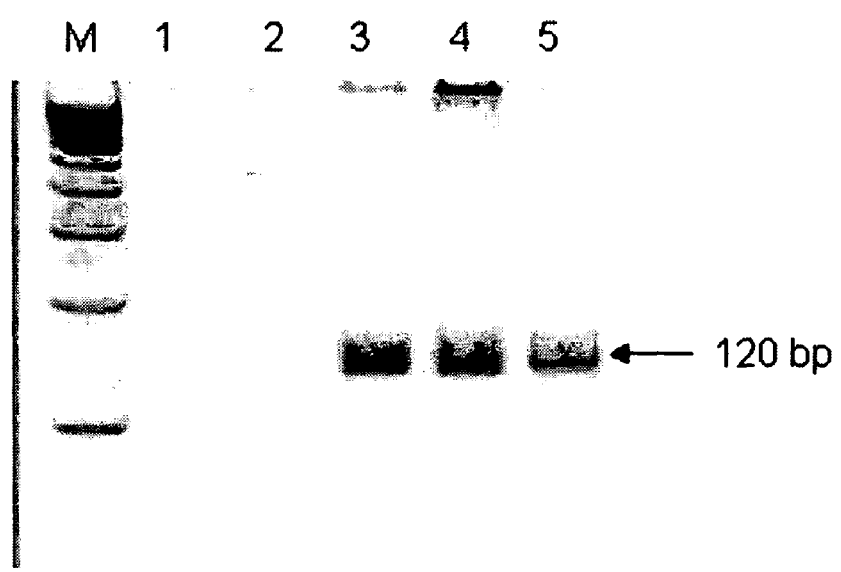
FIG. 5 is a photograph of semi-nested PCR reactions performed on human urine with primers specifc for *Leishmania infantum* sequences resolved by electrophoresis.

FIG. 5 illustrates the electrophoresis of the DNA fragments that were amplified using primers specific for pathogenic *Leishmania* sp
Lane M—DNA molecular weight standards;
Lane 2—Tr-DNA from non-infected subject;
Lane 3—Tr-DNA from an infected patient
Lanes 4 and 5—DNA extracted from blood of infected patients was used as a positive control.
The size of the PCR product is 120 bp (see Table 4).

Example 12

Selection of PCR Primer Sets for the Detection of *Mycobacterium tuberculosis*

PCR primers for the detection of *M. tuberculosis* complex species DNA were selected for the region of IS6110 shown to be highly specific (Hellyer). Primers used in this study are presented in Table 5.

TABLE 5

| ID | Sequence | Product size, bp |
|---|---|---|
| F-785 | ACCAGCACCTAACCGGCTGTGG (SEQ ID NO: 34) | 129 |
| R-913 | CATCGTGGAAGCGACCCGCCAG (SEQ ID NO: 35) | |
| Rn-851 | GTAGGCGAACCCTGCCCAGGTC (SEQ ID NO: 36) | 67 |
| F-489 | GCCCCATCGACCTACTACG (SEQ ID NO: 37) | 330 |
| R-819 | TGAGGTCTGCTACCCACAGC (SEQ ID NO: 38) | |
| Fn-627 | CCCTGAACCGTGAGGGCATCG (SEQ ID NO: 39) | 69 |
| Rn-690 | ACAGGCCGAGTTTGGTCATCAGC (SEQ ID NO: 40) | |

Example 13

Detection of *Mycobacterium tuberculosis* Bacteria DNA Sequences in Urine

All study participants were enrolled at the National Institute for Infectious Diseases (INMI) "L. Spallanzani" in Rome, Italy. In this study we included patients who had been clinically diagnosed with pulmonary tuberculosis as confirmed by isolation of *M. tuberculosis* from sputum culture. Nineteen of the 20 patients had a sputum smear positive for acid-fast bacilli, whereas, only one was HIV positive. No patient exhibited clinical evidence of extra-pulmonary involvement, and all urine cultures for *M. tuberculosis* performed were negative.

Urine specimens were obtained either before or within one week of initiation of anti-tuberculosis therapy. Information regarding age, sex, ethnicity, *M bovis* BCG vaccination, and results of laboratory examinations for tuberculosis were collected. In order to determine whether subsequent therapy had an influence on the ability to detect *M. tuberculosis* DNA, 8 of the patients with pulmonary tuberculosis were asked to return to donate urine specimens two months after initiating anti-tuberculosis therapy. In addition, ten healthy individuals were included as controls in the study.

Urine specimens were processed as described in Examples 1-3 above.

Twenty cycles of PCR amplification were performed as following: isolated DNA equivalent to that contained in 300 μl of urine was added to a 25 μl mixture containing 0.2 μmol/liter of outer primers F-785 and R-913, 5 μl 5×PCR buffer (Promega), 200 μmol/liter dNTP each, and 1 U GoTaq Polymerase (Promega), denatured at 94° C. for 5 minutes followed by 20 cycles of 94° C. for 30 seconds, 62° C. for 30 seconds, 72° C. for 1 minute, and 1 cycle of 72° C. for 5 minutes. 1 μl of the product from this amplification was diluted 1:10 and 1 μl of the dilution was re-amplified 35 cycles using primers F-785 and Rn-851 under the same conditions as in the first reaction. Identical setting was used for the amplification of large, 330 bp fragment. The products from the second amplification were resolved by electrophoresis in 7% polyacrylamide gel, and visualized by ethidium bromide staining.

Figure 6:
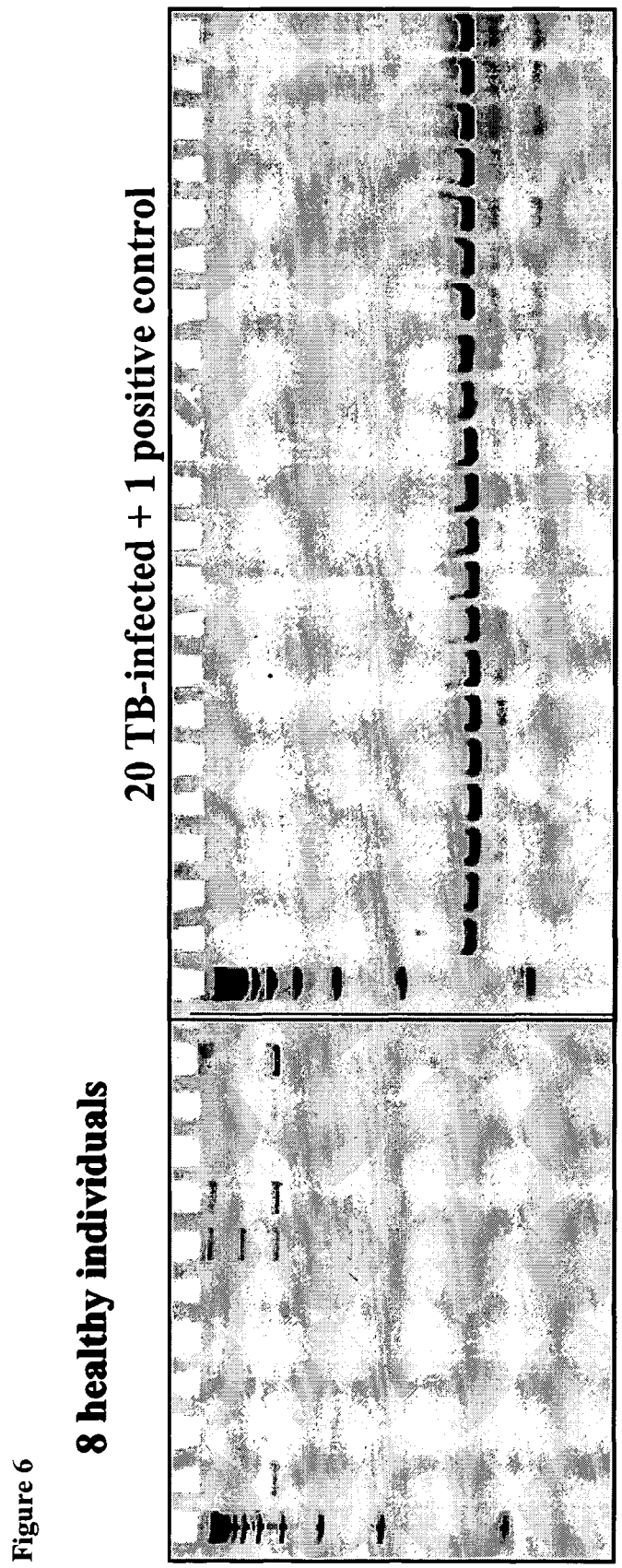
FIG. 6 is a photograph of semi-nested PCR reactions performed on human urine from TB infected and healthy patients with primers specifc for *Mycobacterium tuberculosis* sequences resolved by electrophoresis.

Results from semi-nested amplification are shown in the right panel of FIG. 6. The *M. tuberculosis*-specific product of 67 bp was found in urine specimens from all 20 patients analyzed. Eight healthy individuals used as controls were all found to be negative for the presence of *M. tuberculosis*-specific sequences. The last lane in the gels is the genomic DNA of *Mycobacterium tuberculosis* strain H37RV, as a positive control.

Example 14

Demonstration that TB Specific DNA Sequences Found in Urine Are Cell Free

Previous reports on detection of *M. tuberculosis* DNA in urine employed isolation methods designed to extract high molecular weight DNA from whole urine or urinary sediments. Furthermore, in these reports larger amplicon sizes were used (>200 bp) (Torrea G. J., et al. Med Microbiol. 2005; 54:39-44; Piersimoni C. J., et al. Clin. Microbiol. 40:4138-4142 (2002) Kafwabulula M., et al. Int J Tuberc Lung Dis. 2002; 6:732-7; Marei A. M., et al. J Med Microbiol. 2003 April; 52(Pt 4):331-5. Del Portillo P. et al. J Clin Microbiol. 1991 October; 29(10):2163-8). Therefore, it was important to further characterize the nature of the *M. tuberculosis* Tr-DNA found in urine. In order to address this question, two experimental designs were employed. In the first, specimens were fractionated by centrifuged and DNA was isolated separately from urine sediment and supernatant (see Examples 2 and 3).

Figure 7:
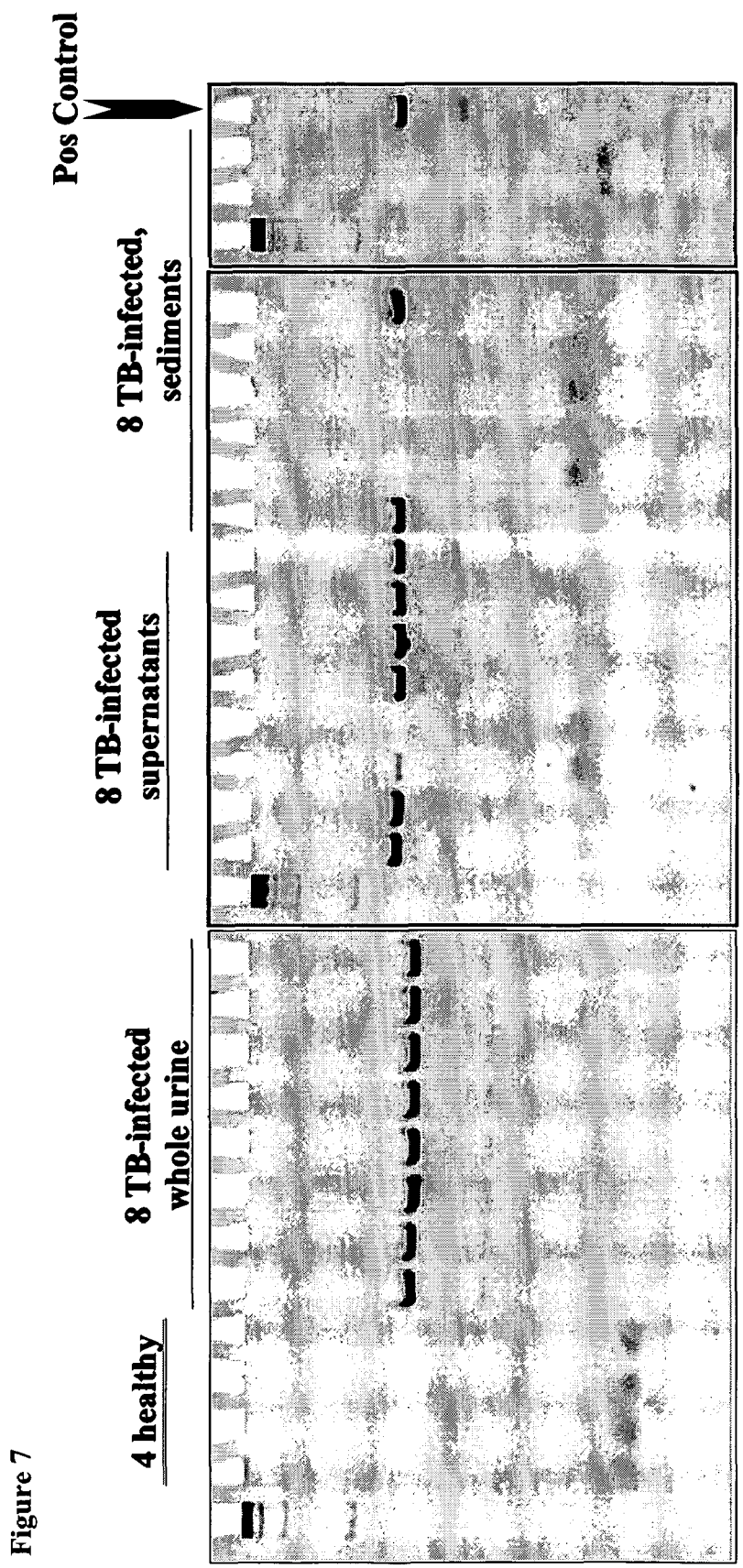
FIG. 7 is a photograph of semi-nested PCR reactions performed on the supernatants and pellets of centrifuged human urine from TB infected and healthy patients before and after treatment with primers specifc for *Mycobacterium tuberculosis* sequences resolved by electrophoresis.

Primer pairs F-785/R-913 and semi-nested primers F-785/Rn-851 specific for short amplicon were used (see Table 5). As shown in FIGS. 7, 6 of 8 of the supernatant samples display the presence of *M. tuberculosis* DNA, whereas only 2 of 8 of the pellet samples were positive.

Figure 8:
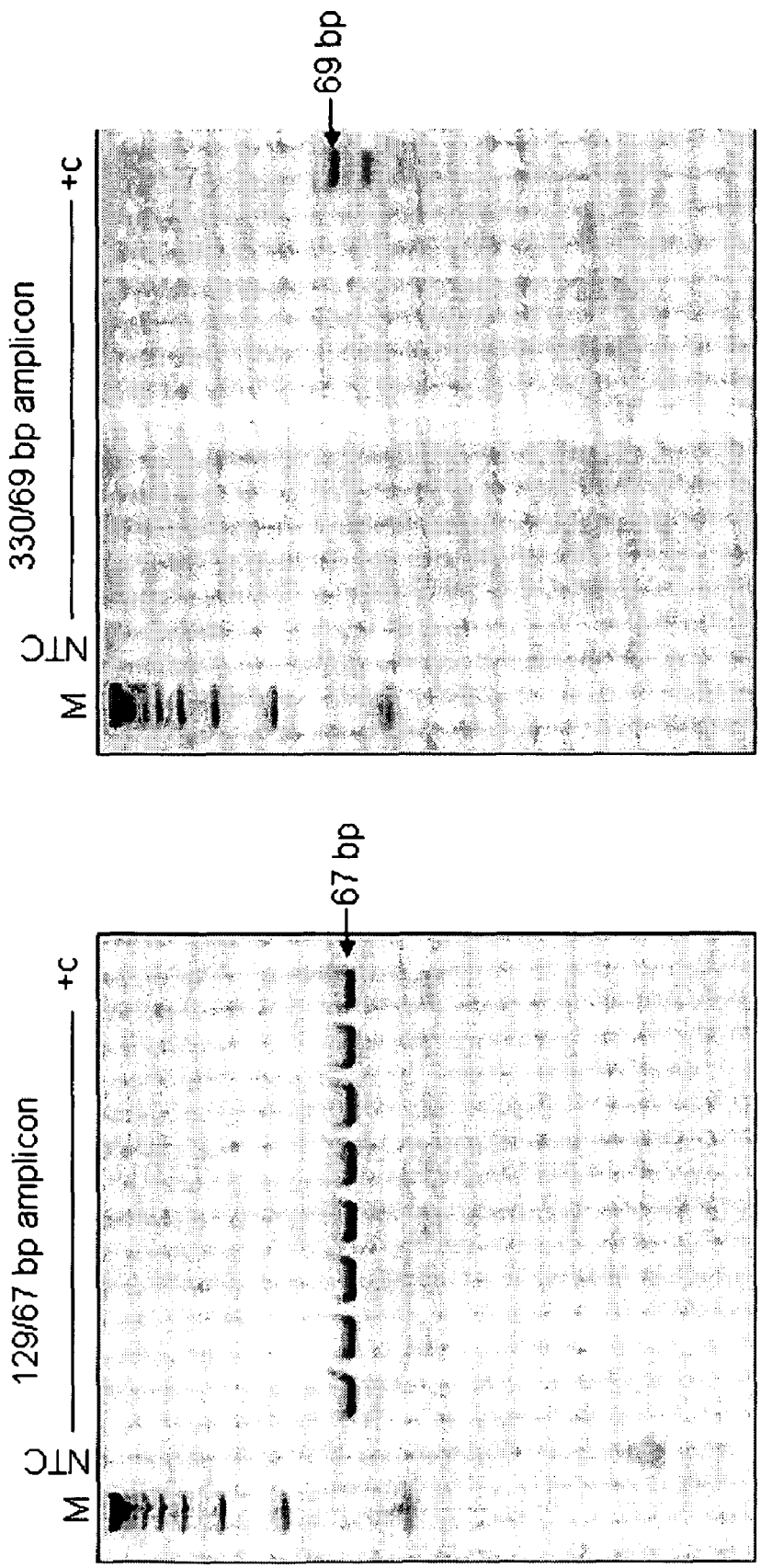
FIG. 8 shows photographs of semi-nested PCR reactions performed on human urine from TB infected patients with primers specific for *Mycobacterium tuberculosis* sequences of 129/67 bp (left panel) and 330/69 bp (right panel) resolved by electrophoresis.

The second experiment was aimed on comparison of PCR products obtained with primers designed for larger amplicon size, in the range used by several other investigators. Results shown in FIG. 8 demonstrate that MTB DNA sequences again were detected in all 7 samples of DNA that had been isolated from urine of pulmonary TB patients when using primers for 129/67 amplicons. However, no PCR products were detected with primers for 330/69 amplicons. In Panel A semi-nested PCR for the short amplicon (target 129 bp). In Panel B semi-nested PCR for the long amplicon with primers F489/R819 (target 330 bp). Respective final semi-nested PCR products for short and long amplicons are 67 bp and 69 bp. Lanes 3-9 represent products of PCR amplification of DNA purified from patients urine. Lanes 1 in both gels show the DNA standards, Lanes 2 in both gels are negative controls, and Lanes 10 in both gels are positive genomic DNA controls. These data confirmed that bacterial DNA fragments extracted from urine are relatively short fragment. Furthermore, these results strongly suggest that it is unlikely that MTB DNA can be reproducibly detected in urine specimens of pulmonary TB patients when using urine sediment PCR analysis combined with large amplicon sizes.

Example 15

Analysis of TB Patients Before and After Treatment

One of the critical problems faced in the management and eradication of pulmonary tuberculosis worldwide is the accurate and early detection of the efficacy of therapeutic treatment of patients. Currently general practice of monitoring of the success of a treatment is based on clinical symptoms, which are relatively late indicators and therefore do not provide information for a "real time" adjustment of the regiment of therapy.

In this regard the impact of Tr-DNA platform technology is twofold. First, it gives a safe, easy and inexpensive means for detection of mutations known to be associated with increased drug resistance, and second, it ideally fits to the early monitoring tasks owing to its inherent capabilities of detection and quantification of non-host origin genetic markers in urine.

Figure 9:
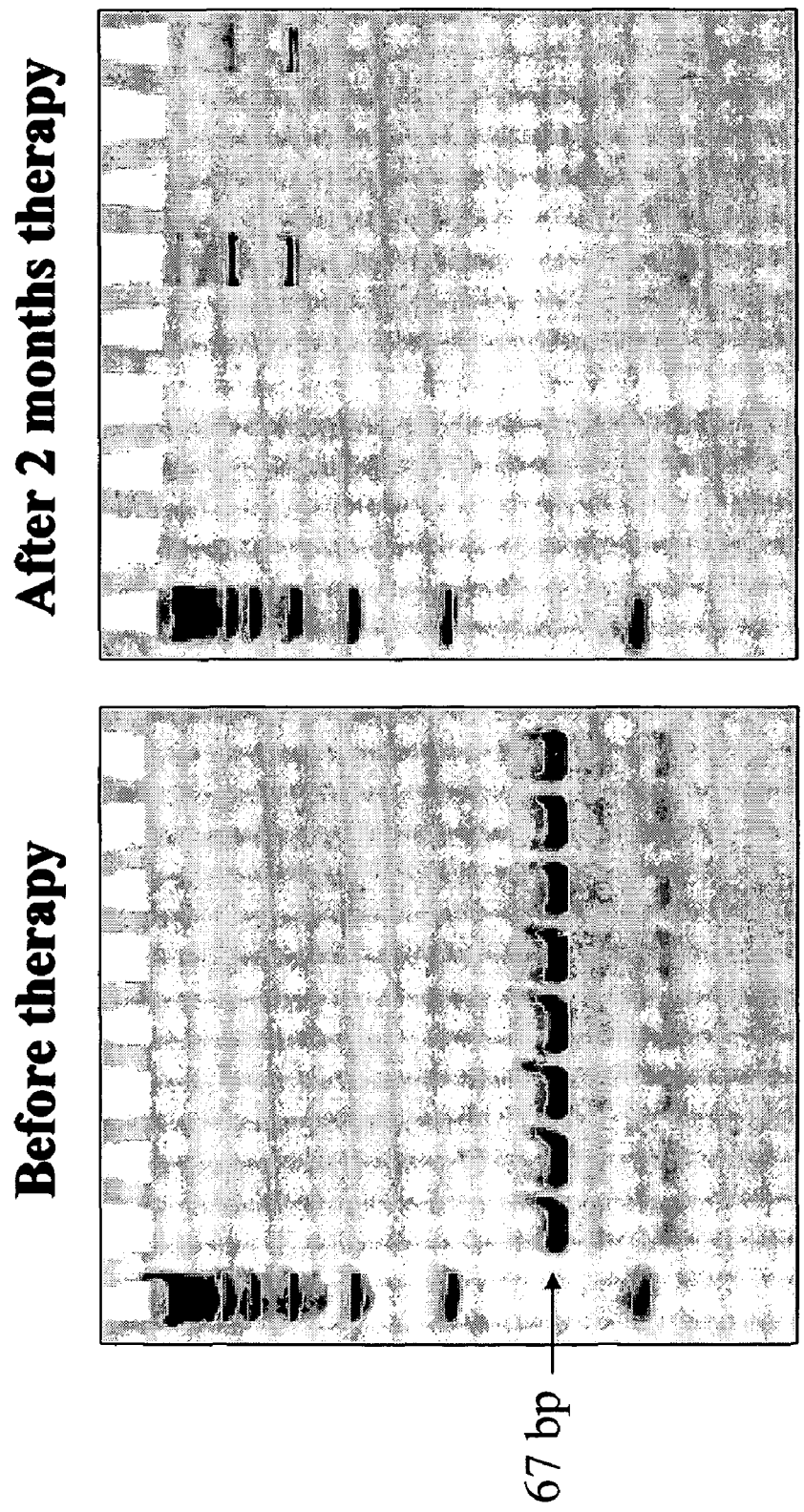
FIG. 9 is a photograph of semi-nested PCR reactions performed on human urine from TB actively infected patients and patients two months after treatment for TB with primers specifc for *Mycobacterium tuberculosis* sequences resolved by electrophoresis.

In order to determine whether MTB-specific DNA sequences in urine can be used for evaluation of therapeutic treatment, 8 of the patients with TB who had been found to be MTB Tr-DNA positive at enrolment were asked to return to donate urine samples approximately two months following initiation of chemotherapy. At the time of the second test clinical symptoms have resolved in these patients and all were sputum smear negative. Tr-DNA extracted from these samples was analyzed and no product corresponding to 67 bp specific TB sequence was observed, as shown in FIG. 9.

Example 16

Selection of PCR Primer Sets for the Detection of *Bacillus anthracis* and Diagnosis of Anthrax A virulent strain of *B. anthracis*, A0843, was used for spore production. This strain, isolated from an outbreak of anthrax, which occurred in Italy, was microbiologically characterized by Turnbull et al. (*Bacillus*, p. 187-210. In M. T. Parker and L. H. Collier (ed.), Topley and Wilson's principles of bacteriology, virology and immunity, VII ed. Edward Arnold, London, United Kingdom 1990), and the presence of plasmids pXO1 and pXO2 has been confirmed by PCR (Fasanella A., et al. (2001) Vaccine 19: 4214-4218; Green B. D., et al. (1985) Infect. Immun. 49:291-297; Ramisse V., et al. (1996). FEMS Microbiol. Lett. 145: 9-16). Genotyping analysis performed by multiple-locus variable-number tandem repeat analysis assigned this strain to the cluster A1a, genotype 3 (Keim, P., et al. (2000). J. Bacteriol. 182: 2928-2936.).

*B. anthracis* infection in rabbits was used as a model system for validation of applicability of Tr-DNA technology for detection of bacterial pathogens and for developing a Tr-DNA assay to diagnose Anthrax infection in human patients. Rabbit represents a more advanced animal model with a disease progression similar to human.

Rabbits were randomly clustered in several groups of 4 animals. Each rabbit was infected by subcutaneous injection of 100,000 spores of the pathogen strain A0843. Animals from each group were sacrificed post-infection at time intervals 6 and 14 hr. After euthanasia urine was harvested from the bladder by syringe aspiration. The volume of collected urine specimens varied from 2 to 10 ml. Four uninfected rabbits were used as controls.

DNA from the rabbit urine specimens were extracted according to the established for the human urine protocol summarized in Examples 1-3 above. Tr-DNA isolated from the urine of 4 non-infected rabbits were used as negative controls.

As targets we have selected pXO1 derived toxicity genetic markers. PCR primers esigned using Beacon Designer software (Premier Biosoft, Palo Alto, Calif.).

TABLE 6

| SEQ ID NO | ID | Sequence | Length (nt) | Tm | Amplicon (bp) |
|---|---|---|---|---|---|
| 41 | LEF_F | GGTTATATGTTCCAGAATCC | 20 | 47.7 | 125 |
| 42 | LEF_R | ATATCCAGCATAATCATCCA | 20 | 48 | |
| 43 | LEF_FN | AAGGTGTAGAATTAAGGAATGATAGTGAG | 29 | 57.8 | 74 |
| 44 | LEF_RN | TCCAGCATAATCATCCACAGCAT | 23 | 57.8 | |
| 45 | CYA_F | AACAACGAAGTACAATACAAGAC | 23 | 53 | 122 |
| 46 | CYA_R | GCTGTTAACGGCTTCAAGA | 19 | 52.6 | |
| 47 | CYA_FSN | AATTGGAGAAATATAGAAGTGATG | 24 | 50.5 | 62 |

TABLE 6-continued

| SEQ ID NO | ID | Sequence | Length (nt) | Tm | Amplicon (bp) |
|---|---|---|---|---|---|
| 48 | PAG_F | AAGTACAAGTGCTGGACCTAC | 21 | 54.5 | 83 |
| 49 | PAG_R | CAACCGTATATCCTTCTACCTCTAA | 25 | 55.3 | |
| 50 | PAG_FSN | TTCCAGACCGTGACAATGATG | 21 | 55.5 | 60 |

Detection of pag specific sequences in urine was carried out by semi-nested PCR using the primer set specific for the pag loci (see Table 6). PCR amplification and electrophoresis analysis was performed per the protocol used in previous Examples. Briefly, twenty cycles of PCR amplification were performed in a 25 µl mixture with primers PAG_F and PAG_R. One µl of the product from this amplification was diluted 1:10 and 1 µl of the dilution was re-amplified 35 cycles using primers PAG_R and PAG_FSN under the same conditions as in the first reaction. The products from the second amplification were resolved by electrophoresis in 7% polyacrylamide gel, and visualized by ethidium bromide staining.

Figure 10:
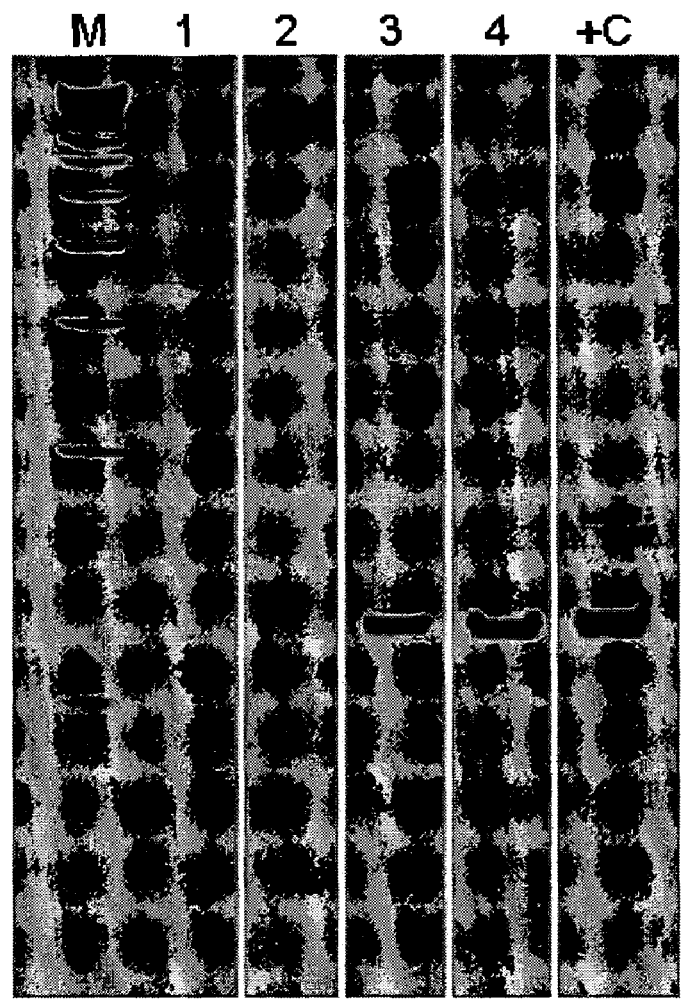
FIG. 10 is a photograph of semi-nested PCR reactions performed on rabbit urine from *B. anthracis* infected and uninfected subjects with primers specifc for *Bacillus anthracis* sequences resolved by electrophoresis.

FIG. 10 shows the detection of *B. anthracis* A0843 specific DNA sequences in the urine of experimentally infected rabbits. Lanes: M—50 bp ladder DNA molecular weight markers; 1—no template control; 2—urine from uninfected rabbit; 3 and 4—urine collected from infected rabbits 6 and 14 hr post-infection, respectively; 5—B. anthracis A0843 genomic DNA, positive control.

We claim:

1. A method for diagnosing a *Mycobacterium tuberculosis* infection in a subject, comprising:
   a) obtaining a urine sample from a subject;
   b) separating a soluble fraction of said urine sample; and
   c) detecting the presence of a cell-free *Mycobacterium tuberculosis* nucleic acid in said soluble fraction of said urine sample, wherein said nucleic acid is less than about 300 bp in length, wherein said detecting is performed by a method selected from the group consisting of PCR, nested PCR, semi-nested PCR, LCR, and SDA, using a primer set comprising at least one forward primer selected from the group consisting of SEQ ID NOs: 34, 37 and 39, and at least one reverse primer selected from the group consisting of SEQ ID NOs: 35, 36, 38 and 40, wherein the presence of said nucleic acid diagnoses a *Mycobacterium tuberculosis* infection.

2. The method of claim 1, further comprising the step of quantitating the nucleic acid.

3. The method of claim 1, wherein the subject is a mammal.

4. The method of claim 3, wherein the mammal is a human.

* * * * *

SEQUENCE LISTING

```
<160> NUMBER OF SEQ ID NOS: 50

<210> SEQ ID NO 1
<211> LENGTH: 22
<212> TYPE: DNA
<213> ORGANISM: Artificial
<220> FEATURE:
<223> OTHER INFORMATION: Primer

<400> SEQUENCE: 1
aagacagtgt tgtgggtgta gg                                              22

<210> SEQ ID NO 2
<211> LENGTH: 18
<212> TYPE: DNA
<213> ORGANISM: artificial
<220> FEATURE:
<223> OTHER INFORMATION: Primer

<400> SEQUENCE: 2
tccaaggccg ctttacac                                                   18

<210> SEQ ID NO 3
<211> LENGTH: 20
<212> TYPE: DNA
<213> ORGANISM: artificial
<220> FEATURE:
<223> OTHER INFORMATION: Primer
```

-continued

<400> SEQUENCE: 3
ggcacaggtt tcatccattc                                          20

<210> SEQ ID NO 4
<211> LENGTH: 25
<212> TYPE: DNA
<213> ORGANISM: artificial
<220> FEATURE:
<223> OTHER INFORMATION: Primer

<400> SEQUENCE: 4
gataggtctc tctttatgtc ttcag                                    25

<210> SEQ ID NO 5
<211> LENGTH: 25
<212> TYPE: DNA
<213> ORGANISM: Artificial
<220> FEATURE:
<223> OTHER INFORMATION: Primer

<400> SEQUENCE: 5
tcrgaaattt gggrmtcagc gttac                                    25

<210> SEQ ID NO 6
<211> LENGTH: 30
<212> TYPE: DNA
<213> ORGANISM: artificial
<220> FEATURE:
<223> OTHER INFORMATION: Primer

<400> SEQUENCE: 6
tccataaaat ttyggatbbd tygggtgttg                               30

<210> SEQ ID NO 7
<211> LENGTH: 22
<212> TYPE: DNA
<213> ORGANISM: artificial
<220> FEATURE:
<223> OTHER INFORMATION: Primer

<400> SEQUENCE: 7
acggatcdtt ttgawgggac ac                                       22

<210> SEQ ID NO 8
<211> LENGTH: 29
<212> TYPE: DNA
<213> ORGANISM: artificial
<220> FEATURE:
<223> OTHER INFORMATION: Primer

<400> SEQUENCE: 8
agcdycayac crcaavaaag tcatgcygc                                29

<210> SEQ ID NO 9
<211> LENGTH: 19
<212> TYPE: DNA
<213> ORGANISM: artificial
<220> FEATURE:
<223> OTHER INFORMATION: Primer

<400> SEQUENCE: 9
ctgadaccgt tcctacagc                                           19

```
<210> SEQ ID NO 10
<211> LENGTH: 24
<212> TYPE: DNA
<213> ORGANISM: artificial
<220> FEATURE:
<223> OTHER INFORMATION: Primer

<400> SEQUENCE: 10
yttyacracc gtgatyattc cagc                                                24

<210> SEQ ID NO 11
<211> LENGTH: 28
<212> TYPE: DNA
<213> ORGANISM: artificial
<220> FEATURE:
<223> OTHER INFORMATION: Primer

<400> SEQUENCE: 11
ckccaaayga tcccatacac agcgagag                                            28

<210> SEQ ID NO 12
<211> LENGTH: 23
<212> TYPE: DNA
<213> ORGANISM: artificial
<220> FEATURE:
<223> OTHER INFORMATION: Primer

<400> SEQUENCE: 12
tgatgggacy aaactcgtaa ccg                                                 23

<210> SEQ ID NO 13
<211> LENGTH: 29
<212> TYPE: DNA
<213> ORGANISM: artificial
<220> FEATURE:
<223> OTHER INFORMATION: Primer

<400> SEQUENCE: 13
cttcattttt taagaacaac tcaccagga                                           29

<210> SEQ ID NO 14
<211> LENGTH: 25
<212> TYPE: DNA
<213> ORGANISM: artificial
<220> FEATURE:
<223> OTHER INFORMATION: Primer

<400> SEQUENCE: 14
accattrgcc tcaatagggg tatgc                                               25

<210> SEQ ID NO 15
<211> LENGTH: 23
<212> TYPE: DNA
<213> ORGANISM: artificial
<220> FEATURE:
<223> OTHER INFORMATION: Primer

<400> SEQUENCE: 15
cactgggcgt aaagagygcg tag                                                 23

<210> SEQ ID NO 16
<211> LENGTH: 21
<212> TYPE: DNA
<213> ORGANISM: artificial
<220> FEATURE:
<223> OTHER INFORMATION: Primer
```

<400> SEQUENCE: 16
ccacctrcct ctcccayact c					21

<210> SEQ ID NO 17
<211> LENGTH: 28
<212> TYPE: DNA
<213> ORGANISM: artificial
<220> FEATURE:
<223> OTHER INFORMATION: Primer

<400> SEQUENCE: 17
ggttaagcca taggatttca cayctgac				28

<210> SEQ ID NO 18
<211> LENGTH: 26
<212> TYPE: DNA
<213> ORGANISM: artificial
<220> FEATURE:
<223> OTHER INFORMATION: Primer

<400> SEQUENCE: 18
gggtattggc ctaacatggc tatgac				26

<210> SEQ ID NO 19
<211> LENGTH: 20
<212> TYPE: DNA
<213> ORGANISM: artificial
<220> FEATURE:
<223> OTHER INFORMATION: Primer

<400> SEQUENCE: 19
aggctccctc tccggaatcg					20

<210> SEQ ID NO 20
<211> LENGTH: 23
<212> TYPE: DNA
<213> ORGANISM: artificial
<220> FEATURE:
<223> OTHER INFORMATION: Primer

<400> SEQUENCE: 20
agaattgggt aatttacgcg cct				23

<210> SEQ ID NO 21
<211> LENGTH: 23
<212> TYPE: DNA
<213> ORGANISM: artificial
<220> FEATURE:
<223> OTHER INFORMATION: Primer

<400> SEQUENCE: 21
cttgatttct tggatggtga tgc				23

<210> SEQ ID NO 22
<211> LENGTH: 24
<212> TYPE: DNA
<213> ORGANISM: artificial
<220> FEATURE:
<223> OTHER INFORMATION: Primer

<400> SEQUENCE: 22
ggttaagatc tcgttcgtta tcgg				24

```
<210> SEQ ID NO 23
<211> LENGTH: 22
<212> TYPE: DNA
<213> ORGANISM: artificial
<220> FEATURE:
<223> OTHER INFORMATION: Primer

<400> SEQUENCE: 23
cggcttaatt tgactcaaca cg                                              22

<210> SEQ ID NO 24
<211> LENGTH: 17
<212> TYPE: DNA
<213> ORGANISM: artificial
<220> FEATURE:
<223> OTHER INFORMATION: Primer

<400> SEQUENCE: 24
agtttyccgc cccggag                                                    17

<210> SEQ ID NO 25
<211> LENGTH: 19
<212> TYPE: DNA
<213> ORGANISM: artificial
<220> FEATURE:
<223> OTHER INFORMATION: Primer

<400> SEQUENCE: 25
cccagtttbc cgccycgga                                                  19

<210> SEQ ID NO 26
<211> LENGTH: 24
<212> TYPE: DNA
<213> ORGANISM: artificial
<220> FEATURE:
<223> OTHER INFORMATION: Primer

<400> SEQUENCE: 26
ctattggaga ttatggagct gtgc                                            24

<210> SEQ ID NO 27
<211> LENGTH: 21
<212> TYPE: DNA
<213> ORGANISM: artificial
<220> FEATURE:
<223> OTHER INFORMATION: Primer

<400> SEQUENCE: 27
cacacaccga accgargttg c                                               21

<210> SEQ ID NO 28
<211> LENGTH: 21
<212> TYPE: DNA
<213> ORGANISM: artificial
<220> FEATURE:
<223> OTHER INFORMATION: Primer

<400> SEQUENCE: 28
gggagaacgt actggggcgt c                                               21

<210> SEQ ID NO 29
<211> LENGTH: 21
<212> TYPE: DNA
<213> ORGANISM: artificial
<220> FEATURE:
<223> OTHER INFORMATION: Primer
```

```
<400> SEQUENCE: 29
tcgctgtagt tcgtcttggt g                                               21

<210> SEQ ID NO 30
<211> LENGTH: 24
<212> TYPE: DNA
<213> ORGANISM: artificial
<220> FEATURE:
<223> OTHER INFORMATION: Primer

<400> SEQUENCE: 30
ctgttgctgt taaagggttc gtag                                            24

<210> SEQ ID NO 31
<211> LENGTH: 21
<212> TYPE: DNA
<213> ORGANISM: artificial
<220> FEATURE:
<223> OTHER INFORMATION: Primer

<400> SEQUENCE: 31
tccgacatgg acgggacgac c                                               21

<210> SEQ ID NO 32
<211> LENGTH: 18
<212> TYPE: DNA
<213> ORGANISM: artificial
<220> FEATURE:
<223> OTHER INFORMATION: Primer
<300> PUBLICATION INFORMATION:
<301> AUTHORS: A Belli et al.
<302> TITLE: Simplified polymerase chain reaction detection of new world
      Leishmania in clinical specimens of cutaneous leishmaniasis
<303> JOURNAL: Am. J. Trop. Med. Hyg.
<304> VOLUME: 58
<305> ISSUE: 1
<306> PAGES: 102-109
<307> DATE: 1998

<400> SEQUENCE: 32
gtgggggagg ggcgttct                                                   18

<210> SEQ ID NO 33
<211> LENGTH: 21
<212> TYPE: DNA
<213> ORGANISM: artificial
<220> FEATURE:
<223> OTHER INFORMATION: Primer
<300> PUBLICATION INFORMATION:
<301> AUTHORS: A Belli et al.
<302> TITLE: Simplified polymerase chain reaction detection of new world
      Leishmania in clinical specimens of cutaneous Leishmaniasis
<303> JOURNAL: Am. J. Trop. Med. Hyg.
<304> VOLUME: 58
<305> ISSUE: 1
<306> PAGES: 102-109
<307> DATE: 1998

<400> SEQUENCE: 33
attttacacc aaccccagt t                                                21

<210> SEQ ID NO 34
<211> LENGTH: 22
<212> TYPE: DNA
<213> ORGANISM: artificial
<220> FEATURE:
<223> OTHER INFORMATION: Primer
```

```
<400> SEQUENCE: 34
accagcacct aaccggctgt gg                                              22

<210> SEQ ID NO 35
<211> LENGTH: 22
<212> TYPE: DNA
<213> ORGANISM: artificial
<220> FEATURE:
<223> OTHER INFORMATION: Primer

<400> SEQUENCE: 35
catcgtggaa gcgacccgcc ag                                              22

<210> SEQ ID NO 36
<211> LENGTH: 22
<212> TYPE: DNA
<213> ORGANISM: artificial
<220> FEATURE:
<223> OTHER INFORMATION: Primer

<400> SEQUENCE: 36
gtaggcgaac cctgcccagg tc                                              22

<210> SEQ ID NO 37
<211> LENGTH: 19
<212> TYPE: DNA
<213> ORGANISM: artificial
<220> FEATURE:
<223> OTHER INFORMATION: Primer

<400> SEQUENCE: 37
gccccatcga cctactacg                                                  19

<210> SEQ ID NO 38
<211> LENGTH: 20
<212> TYPE: DNA
<213> ORGANISM: artificial
<220> FEATURE:
<223> OTHER INFORMATION: Primer

<400> SEQUENCE: 38
tgaggtctgc tacccacagc                                                 20

<210> SEQ ID NO 39
<211> LENGTH: 21
<212> TYPE: DNA
<213> ORGANISM: Artificial
<220> FEATURE:
<223> OTHER INFORMATION: Primer

<400> SEQUENCE: 39
ccctgaaccg tgagggcatc g                                               21

<210> SEQ ID NO 40
<211> LENGTH: 23
<212> TYPE: DNA
<213> ORGANISM: artificial
<220> FEATURE:
<223> OTHER INFORMATION: Primer

<400> SEQUENCE: 40
acaggccgag tttggtcatc agc                                             23
```

```
<210> SEQ ID NO 41
<211> LENGTH: 20
<212> TYPE: DNA
<213> ORGANISM: artificial
<220> FEATURE:
<223> OTHER INFORMATION: primer

<400> SEQUENCE: 41
ggttatatgt tccagaatcc                                              20

<210> SEQ ID NO 42
<211> LENGTH: 20
<212> TYPE: DNA
<213> ORGANISM: artificial
<220> FEATURE:
<223> OTHER INFORMATION: Primer

<400> SEQUENCE: 42
atatccagca taatcatcca                                              20

<210> SEQ ID NO 43
<211> LENGTH: 29
<212> TYPE: DNA
<213> ORGANISM: artificial
<220> FEATURE:
<223> OTHER INFORMATION: Primer

<400> SEQUENCE: 43
aaggtgtaga attaaggaat gatagtgag                                    29

<210> SEQ ID NO 44
<211> LENGTH: 23
<212> TYPE: DNA
<213> ORGANISM: artificial
<220> FEATURE:
<223> OTHER INFORMATION: Primer

<400> SEQUENCE: 44
tccagcataa tcatccacag cat                                          23

<210> SEQ ID NO 45
<211> LENGTH: 23
<212> TYPE: DNA
<213> ORGANISM: artificial
<220> FEATURE:
<223> OTHER INFORMATION: Primer

<400> SEQUENCE: 45
aacaacgaag tacaatacaa gac                                          23

<210> SEQ ID NO 46
<211> LENGTH: 19
<212> TYPE: DNA
<213> ORGANISM: artificial
<220> FEATURE:
<223> OTHER INFORMATION: Primer

<400> SEQUENCE: 46
gctgttaacg gcttcaaga                                               19

<210> SEQ ID NO 47
<211> LENGTH: 24
<212> TYPE: DNA
<213> ORGANISM: artificial
<220> FEATURE:
<223> OTHER INFORMATION: Primer
```

```
<400> SEQUENCE: 47
aattggagaa atatagaagt gatg                                              24

<210> SEQ ID NO 48
<211> LENGTH: 21
<212> TYPE: DNA
<213> ORGANISM: artificial
<220> FEATURE:
<223> OTHER INFORMATION: Primer

<400> SEQUENCE: 48
aagtacaagt gctggaccta c                                                 21

<210> SEQ ID NO 49
<211> LENGTH: 25
<212> TYPE: DNA
<213> ORGANISM: artificial
<220> FEATURE:
<223> OTHER INFORMATION: Primer

<400> SEQUENCE: 49
caaccgtata tccttctacc tctaa                                             25

<210> SEQ ID NO 50
<211> LENGTH: 21
<212> TYPE: DNA
<213> ORGANISM: artificial
<220> FEATURE:
<223> OTHER INFORMATION: primer

<400> SEQUENCE: 50
ttccagaccg tgacaatgat g                                                 21
```